United States Patent
Phillips et al.

(10) Patent No.: US 9,878,155 B1
(45) Date of Patent: Jan. 30, 2018

(54) METHOD FOR NEUROSTIMULATION ENHANCED TEAM PERFORMANCE

(71) Applicant: HRL Laboratories, LLC, Malibu, CA (US)

(72) Inventors: Matthew E. Phillips, Calabasas, CA (US); Matthias Ziegler, Oakton, VA (US)

(73) Assignee: HRL Laboratories, LLC, Mailbu, CA (US)

( * ) Notice: Subject to any disclaimer, the term of this patent is extended or adjusted under 35 U.S.C. 154(b) by 0 days.

(21) Appl. No.: 15/250,150

(22) Filed: Aug. 29, 2016

Related U.S. Application Data

(63) Continuation-in-part of application No. 14/987,467, filed on Jan. 4, 2016, which is a continuation-in-part of application No. 15/219,023, filed on Jul. 25, 2016.

(60) Provisional application No. 62/099,835, filed on Jan. 5, 2015, provisional application No. 62/196,155, filed on Jul. 23, 2015, provisional application No. 62/210,976, filed on Aug. 27, 2015.

(51) Int. Cl.
*A61N 1/36* (2006.01)
*A61B 5/0476* (2006.01)
*A61B 5/00* (2006.01)
*A61B 5/16* (2006.01)

(52) U.S. Cl.
CPC ........ *A61N 1/36025* (2013.01); *A61B 5/0075* (2013.01); *A61B 5/0476* (2013.01); *A61B 5/16* (2013.01); *A61B 5/4836* (2013.01)

(58) Field of Classification Search
CPC .................. A61N 1/36025; A61N 2001/36039
See application file for complete search history.

(56) References Cited

U.S. PATENT DOCUMENTS

| | | | |
|---|---|---|---|
| 2016/0008632 A1* | 1/2016 | Wetmore | A61N 7/00 601/2 |
| 2016/0038049 A1* | 2/2016 | Geva | A61B 5/048 600/544 |

OTHER PUBLICATIONS

Merzagora, A. C., Foffani, G., Panyavin I., Mordillo-Mateos, L., Aguilar, J., Onaral, B. and A. Oliviero. (2010). Prefrontal hemodynamic changes produced by anodal direct current stimulation. Neuroimage, 49, 3: pp. 2304-2310.

(Continued)

*Primary Examiner* — Eric D Bertram
(74) *Attorney, Agent, or Firm* — Tope-McKay & Associates

(57) ABSTRACT

Described is a system for augmenting team performance via individual neurostimulation. An assessment is generated for each team member of a team while the team member is performing a behavioral task using neuroimaging data. A target brain state is selected in team members for team performance enhancement. The target brain state is associated with specific brain regions, and the system determines a HD-tCS neurostimulation needed to reach the specific brain regions to induce the target brain state in the team members. The determined HD-tCS neurostimulation is applied to the team members while simultaneously sensing, via real-time neuroimaging, neural activity in each team member while the team member performs a behavioral task. Team performance is enhanced by adjusting the HD-tCS neurostimulation of each team member, based on the sensed neural activity, to direct each team member toward the target brain state.

24 Claims, 14 Drawing Sheets
(2 of 14 Drawing Sheet(s) Filed in Color)

(56) References Cited

OTHER PUBLICATIONS

Bikson, M., Rahman, A., and Datta, A. (2012). Computational models of transcranial direct current stimulation. Clinical EEG and Neuroscience, 43, 3: pp. 176-183.

Molaee-Ardekani, B., Márquez-Ruiz, J., Merlet, I., Leal-Campanario, R., Gruart, A., Sánchez-Campusano, R., and Wendling, F. (2012). Effects of transcranial Direct Current Stimulation (tDCS) on cortical activity: A computational modeling study. Brain stimulation. pp. 25-39.

Norman, K. A. and O'Reilly, R. C. (2003). Modeling hippocampal and neocortical contributions to recognition memory: a complementary-learning-systems approach. Psychological review, 110, 4: pp. 611-646.

Anderson, J. R., Bothell, D., Byrne, M. D., Douglass, S., Lebiere, C., and Qin, Y. (2004). An integrated theory of the mind. Psychological review, 111, 4: pp. 1036-1060.

Antal, A. and Paulus, W. (2008). Transcranial direct current stimulation and visual perception. Perception, 37, 3: pp. 367-374.

Hasan Ayaz, M.P., Cakir, K., Izzetoglu, Curtin, A., Shewokis, P.A., Bunce S. C., and Onaral, B. (2012). Monitoring expertise development during simulated uav piloting tasks using optical brain imaging. Aerospace Conference. 2012 IEEE, pp. 1-11.

Siwei, Bai, Loo, C., and Dokos. S. A review of computational models of transcranial electrical stimulation. (2013). Critical Reviewsim in Biomedical Engineering, pp. 21-35.

Boggio, P.S., Ferrucci, R., Rigonafii, S.P., Covre, P., Nitsche, M., Pascual-Leone, A., and Fregni, F. (2006). Effects of transcranial direct current stimulation on working memory in patients with parkinson's disease. Journal of the neurological sciences, 249, 1: pp. 31-38.

Borckardt, J.J., Bikson, M., Frohman, H., Reeves, S. T., Datta, A., Bansal, V., Madan, A., Barth, K., and George, M. S. (2012). A pilot study of the tolerability and effects of high-definition transcranial direct current stimulation (hd-tdcs) on pain perception. The Journal of Pain, 13, 2: pp. 112-120.

Borst, J. P. and Anderson, J.R. (2013). Using model-based functional mri to locate working memory updates and declarative memory retrievals in the fronto-parietal network. Proceedings of the National Academy of Sciences, 110, 5: pp. 1628-1633.

Brunstein, A., Betts, S., and Anderson, J.A. (2009). Practice enables successful learning under minimal guidance. Journal of Educational Psychology, 101, 4: pp. 790-802.

Chi, R.P. and Snyder, A.W. (2011). Facilitate insight by non-invasive brain stimulation. PLoS One, 6, 2:e16655, pp. 1-7.

Chrysikou, E.G., Hamilton, R.H., Coslett, H.B., Datta, A., Bikson, M., and Thompson-Schill, S.L. (2013). Noninvasive transcranial direct current stimulation over the left prefrontal cortex facilitates cognitive flexibility in tool use. Cognitive Neuroscience, (ahead-of-print): pp. 1-9.

Daily, L.Z., Lovett, M.C., and Reder, L.M. (2001). Modeling individual differences in working memory performance: A source activation account. Cognitive Science, 25, 3: pp. 315-353.

Datta, A., Bansal, V., Diaz, J., Patel, J., Reato, D., and Bikson, M. (2009). Gyri-precise head model of transcranial direct current stimulation: improved spatial focality using a ring electrode versus conventional rectangular pad. Brain stimulation, 2, 4: pp. 201-207.

Datta, A., Truong, D., Minhas. P., Parra, L.C., and Bikson, M. (2012). Inter-individual variation during transcranial direct current stimulation and normalization of dose using mri-derived computational models. Frontiers in Psychiatry, 3, pp. 1-8.

Dayan, E., Censor, N., Buch, E.R., Sandrini, M., and Cohen, L.G. (2013). Noninvasive brain stimulation: from physiology to network dynamics and back. Nature neuroscience, 16, 7: pp. 838-844.

Dipoppa, M. and Gutkin, B.S. (2013). Flexible frequency control of cortical oscillations enables computations required for working memory. Proceedings of the National Academy of Sciences, pp. 12828-12833.

Dmochowski, J.P., Datta, A., Bikson, M., Su, Y., and Parra, L.C. (2011). Optimized multi-electrode stimulation increases focality and intensity at target. Journal of neural engineering, 8, 4:046011, pp. 1-16.

Dockery, C.A., Hueckel-Weng, R., Birbaumer, N., and Plewnia, C. (2009). Enhancement of planning ability by transcranial direct current stimulation. The Journal of Neuroscience, 29, 22: pp. 7271-7277.

Edwards, D., Cortes, M., Datta, A., Minhas, P., Wassermann, E. M., and Bikson, M. (2013). Physiological and modeling evidence for focal transcranial electrical brain stimulation in humans: a basis for high-definition tdcs. NeuroImage, pp. 266-275.

Falcone, B., Coffman, B.A., Clark, V.P., and Parasuraman, R. (2012). Transcranial direct current stimulation augments perceptual sensitivity and 24-hour retention in a complex threat detection task. PloS one, 7, 4:e34993, pp. 1-10.

Fregni, F., Boggio, P.S., Nitsche, M., Bermpohl, F., Antal, A., Feredoes, E., Marcolin, M.A., Rigonatti, S.P., Silva, M.T.A., Paulus, W., et al. (2005). Anodal transcranial direct current stimulation of prefrontal cortex enhances working memory. Experimental Brain Research, 166, 1: pp. 23-30.

Hauser, T.U., Rotzer, S., Grabner, R.H., Mérillat, S., and Jäncke, L. (2013). Enhancing performance in numerical magnitude processing and mental arithmetic using transcranial direct current stimulation (tdcs). Frontiers in human neuroscience, 7, pp. 1-9.

Huppert, T.J., Diamond, S.G., Franceschini, M.A., and Boas, D.A. (2009). Homer: a review of time-series analysis methods for near-infrared spectroscopy of the brain. Applied optics, 48, 10: pp. D280-D298.

Izzetoglu, M., Izzetoglu, K., Bunce, S., Ayaz, H., Devaraj, A., Onaral, B., and Pourrezaei, K. (2005). Functional near-infrared neuroimaging. Neural Systems and Rehabilitation Engineering, IEEE Transactions on, 13, 2: pp. 153-159.

Jaeggi, S.M., Buschkuehl, M., Jonides, J., and Perrig, W.J. (2008). Improving fluid intelligence with training on working memory. Proceedings of the National Academy of Sciences, 105, 19: pp. 6829-6833.

Jung-Beeman, M., Bowden, E.M., Haberman, J., Frymiare, J.L., Arambel-Liu, S., Greenblatt, R., Reber, P.J., and Kounios, J. (2004). Neural activity when people solve verbal problems with insight. PLoS biology, 2, 4:e97, pp. 3500-1-0500-11.

Juvina, I., Jastrzembski, T.S., and McKinley, A. "When to apply brain stimulation to achieve learning acceleration," ICCM Conference 2013, pp. 358-363.

Kohno, S., Miyai, I., Seiyama, A., Oda, I., Ishikawa, A., Tsuneishi, S., Takashi Amita, T., and Shimizu, K. (2007). Removal of the skin blood flow artifact in functional near-infrared spectroscopic imaging data through independent component analysis. Journal of biomedical optics, 12, 6:062111-1-062111-9.

Kounios, J. and Beeman, M. (2013). The cognitive neuroscience of insight. Annual Review of Psychology, 65, 1, pp. 210-216.

Kounios, J., Fleck, J.I., Green, D.L., Payne, L., Stevenson, J.L., Bowden, E.M., and Jung-Beeman, M. (2008). The origins of insight in resting-state brain activity. Neuropsychologia, 46, 1: pp. 281-291.

Kounios, J., Frymiare, J.L., Bowden, E.M., Fleck, J.I., Subramaniam, K., Parrish, T.B., and Jung-Beeman, M. (2006). The prepared mind neural activity prior to problem presentation predicts subsequent solution by sudden insight. Psychological Science, 17, 10: pp. 882-890.

Kuo, H-I., Bikson, M., Datta, A., Minhas, P., Paulus, W., Kuo, M-F., and Nitsche, M.A. (2012). Comparing cortical plasticity induced by conventional and high-definition 4x 1 ring tdcs: a neurophysiological study. Brain stimulation, pp. 644-648.

Lebiere, C., Pirolli, P., Thomson, R., Paik, J., Rutledge-Taylor, M., James Staszewski, and Anderson, J.R. (2013). A functional model of sensemaking in a neurocognitive architecture. Computational Intelligence and Neuroscience, 2013: e921695, pp. 1-29.

Lefebvre, S., Laloux, P., Peeters, A., Desfontaines, P., Jamart, J., and Vandermeeren, Y. (2012). Dual-tdcs enhances online motor skill learning and long-term retention in chronic stroke patients. Frontiers in human neuroscience, 6, pp. 1-17.

Lehman, J., Laird, J., and Rosenbloom, P. (2006). A gentle introduction to soar, an architcture for human cognition, pp. 1-47.

(56) References Cited

OTHER PUBLICATIONS

Leite, J., Carvalho, S., Fregni, F., and Gonsalves, O.F. (2011). Task-specific effects of tdcs-induced cortical excitability changes on cognitive and motor sequence set shifting performance. PloS one, 6, 9:e24140, pp. 1-9.

Leon P.S., Knock, S.A., Woodman, M.M., Domide, L., Mersmann, J., McIntosh, A.R., and Jirsa, V. (2013). The Virtual Brain: a simulator of primate brain network dynamics. Frontiers in Neuroinformatics, 7, pp. 1-23.

Lupyan, G., Mirman, D. Hamilton, R., & Thompson-Schill, S. L. (2012). Categorization is modulated by transcranial direct current stimulation over left prefrontal cortex. Cognition, 124, 1: pp. 36-49.

Meiron, O. and Lavidor, M. (2013). Prefrontal oscillatory stimulation modulates access to cognitive control references in retrospective metacognitive commentary. Clinical Neurophysiology, pp. 77-82.

Melby-Lervåg, M. and Hulme, C. (2013). Is working memory training effective? a meta-analytic review. Developmental Psychology, 49, 2:pp. 270-291.

Metuki, N., Sela, T., and Lavidor, M. (2012). Enhancing cognitive control components of insight problems solving by anodal tdcs of the left dorsolateral prefrontal cortex. Brain Stimulation, 5, 2: pp. 110-115.

Miller, E. K. and Cohen, J.D. (2001). An integrative theory of prefrontal cortex function. Annual review of neuroscience, 24, 1: pp. 167-202.

Noudoost, B. and Moore, T. (2013). Parietal and prefrontal neurons driven to distraction. Nature Neuroscience, 16, 1: pp. 8-9.

Nozari, N. and Thompson-Schill, S. (2013). More attention when speaking: does it help or does it hurt?, Neuropsychologia 51, pp. 2770-2780.

Pirulli, C., Fertonani, A., and Miniussi, C. (2013). The role of timing in the induction of neuromodulation in perceptual learning by transcranial electric stimulation. Brain stimulation 6, pp. 683-689.

Snowball, A., Tachtsidis, I., Popescu, T., Thompson, J., Delazer, M., Zamarian, L., Zhu, T., and Kadosh, R. C. (2013). Long-term enhancement of brain function and cognition using cognitive training and brain stimulation. Current Biology 23, pp. 987-992.

Soekadar, S.R., Witkowski, M., Cossio, E.G., Birbaumer, N., Robinson, S.E., and Cohen, L.G. (2013). In vivo assessment of human brain oscillations during application of transcranial electric currents. Nature Communications, 4, pp. 1-10.

Sparing, R., Thimm, M., Hesse, M.D., Küst, J., Karbe, H., and Fink, G.R. (2009). Bidirectional alterations of interhemispheric parietal balance by non-invasive cortical stimulation. Brain, 132, 11: pp. 3011-3020.

Stocco, A. and Anderson, J.R. (2008). Endogenous control and task representation: An fmri study in algebraic problem solving. Journal of Cognitive Neuroscience, 20, 7: pp. 1300-1314.

Stocco, A., Lebiere, C., and Anderson, J.R. (2010). Conditional routing of information to the cortex: A model of the basal ganglia's role in cognitive coordination. Psychological Review, 117, 2: pp. 540-574.

Subramaniam, K., Kounios, J., Parrish, T.B., and Jung-Beeman, M. (2009). A brain mechanism for facilitation of insight by positive affect. Journal of Cognitive Neuroscience, 21, 3: pp. 415-432.

Truong, D.Q., Magerowski, G., Blackburn, G.L., Bikson, and Alonso-Alonso, M. (2013) Computational modeling of transcranial direct current stimulation (tdcs) in obesity: impact of head fat and dose guidelines. NeuroImage: Clinical 2, pp. 759-766.

Villamar, M.F., Wivatvongvana, P., Patumanond, J., Bikson, M., Truong, D.Q., Datta, A., and Fregni, F. (2013). Focal modulation of the primary motor cortex in fibromyalgia using 4×1-ring high-definition transcranial direct current stimulation (HD-tDCS): immediate and delayed analgesic effects of cathodal and anodal stimulation. The Journal of Pain, pp. 371-383.

Wallach, D. and Lebiere, C. (2003). Implicit and explicit learning in a unified architecture of cognition, In L. Jimenez, editor, Attention and Implicit Learning. John Benjamins, Amsterdam, Netherlands, pp. 215-250.

Javadi, A. H., & Walsh, V. (2012). Transcranial direct current stimulation (tDCS) of the left dorsolateral prefrontal cortex modulates declarative memory. Brain Stimulation, 5(3), pp. 231-241.

Datterson, F., Jepson, C., Strasser, A.A., Loughead, J., Perkins, K.A., Gur, R.C., Frey, J.M., Siegel, S., and Lerman, C. (2009). Varenicline improves mood and cognition during smoking abstinence. Biological Psychiatry, 65, 2: pp. 144-149.

Ahmed, Amir, IA, Ali, A., Kramers, C., Härmark, L., Burger, D.M., and Verhoeven, W. (2013). Neuropsychiatric adverse events of varenicline: a systematic review of published reports. Journal of Clinical Psychopharmacology, 33, 1: pp. 55-62.

Haddal & Gertler. (2010) Homeland Security: Unmanned Aerial Vehicles and Boarder Surveillance. Congressional Research Service Report for Congress. pp. 1-7.

Attrition: Pilots Despise Flying UAVs. h t t p : / / w w w . strategypage.com/htmw/htatrit/articles/20120812.aspx. Taken on Apr. 14, 2016.

No One Wants to be a Drone Pilot, U.S. Air Force Discovers. h t t p : / / w w w .popsci.com/technology/article/2013-08/air-force-drone-program-too-unmanned-its-own-good. Taken on Apr. 14, 2016.

Performance Management. h t t p : / / w w w .opm.gov/policy-data-oversight/performance-management/reference-materials/historical/facts-about-measuring-team-performance. Taken on Apr. 14, 2016.

Konvalinka, I., & Roepstorff, A. (2012). The two-brain approach: how can mutually interacting brains teach us something about social interaction? Frontiers in Human Neuroscience, 6, pp. 1-10.

Bell, Anthony J., and Terrence J. Sejnowski. (1995). "An information-maximization approach to blind separation and blind deconvolution." Neural computation 7, No. 6: pp. 1129-1159.

http://en.wikipedia.org/wiki/AAI_RQ-7_Shadow Downloaded on Oct. 24, 2016.

Robert J Sternberg and Janet E Davidson. The nature of insight. The MIT Press, 1995. Chapter 6: 6. Cognitive and Affective Components of Insight, pp. 197-226.

Albert Snowball, Ilias Tachtsidis, Tudor Popescu, Jacqueline Thompson, Margarete Delazer, Laura Zamarian, Tingting Zhu, and Roi Cohen Kadosh. "Long-term enhancement of brain function and cognition using cognitive training and brain stimulation." Current Biology 23, pp. 987-992, Jun. 3, 2013.

Surjo R Soekadar, Matthias Witkowski, Eliana G Cossio, Niels Birbaumer, Stephen E Robinson, and Leonardo G Cohen. "In vivo assessment of human brain oscillations during application of transcranial electric currents." Nature Communications (2013), 4:2032, DOI: 10.1038/ncomms3032, pp. 1-10.

R Sparing, M Thimm, MD Hesse, J Küst, H Karbe, and GR Fink. "Bidirectional alterations of interhemispheric parietal balance by non-invasive cortical stimulation." Brain, 132(11): pp. 3011-3020, 2009.

A. Stocco and J. R Anderson. "Endogenous control and task representation: An fmri study in algebraic problem solving." Journal of Cognitive Neuroscience, 20(7): pp. 1300-1314, 2008.

A. Stocco, C. Lebiere, and J. R. Anderson. "Conditional routing of information to the cortex: A model of the basal ganglia's role in cognitive coordination." Psychological Review, 117(2): pp. 540-574, 2010.

Karuna Subramaniam, John Kounios, Todd B Parrish, and Mark Jung-Beeman. "A brain mechanism for facilitation of insight by positive affect." Journal of Cognitive Neuroscience, 21(3): pp. 415-432, 2009.

Dennis Q Truong, Greta Magerowski, George L Blackburn, Marom Bikson, and Miguel Alonso-Alonso. "Computational modeling of transcranial direct current stimulation (tdcs) in obesity: impact of head fat and dose guidelines." NeuroImage: Clinical 2 (2013), pp. 759-766.

Mauricio F Villamar, Pakorn Wivatvongvana, Jayanton Patumanond, Marom Bikson, Dennis Q Truong, Abhishek Datta, and Felipe Fregni. "Focal modulation of the primary motor cortex in fibromyalgia using 4×1-ring high-definition transcranial direct current stimulation (HD-tDCS): immediate and delayed analgesic effects of cathodal and anodal stimulation." The Journal of Pain, vol. 14, No. 4 (April), 2013: pp. 371-383.

(56) References Cited

OTHER PUBLICATIONS

Dieter Wallach and Christian Lebiere, "Implicit and explicit learning in a unified architecture of cognition" In Jimenez, Luis, ed. Attention and Implicit Learning.. Philadelphia, PA, USA: John Benjamins Publishing Company, 2003, pp. 215-250.
Javadi, A. H., & Walsh, V. (2012). "Transcranial direct current stimulation (tDCS) of the left dorsolateral prefrontal cortex modulates declarative memory." Brain Stimulation, 5(3), pp. 231-241.
Patterson, Freda, Christopher Jepson, Andrew A. Strasser, James Loughead, Kenneth A. Perkins, Ruben C. Gur, Joseph M. Frey, Steven Siegel, and Caryn Lerman. "Varenicline improves mood and cognition during smoking abstinence." Biological Psychiatry 65, No. 2 (2009): pp. 144-149.
Ahmed, Amir IA, Abdullah NA Ali, Cees Kramers, Linda VD Härmark, David M. Burger, and Willem MA Verhoeven. "Neuropsychiatric adverse events of varenicline: a systematic review of published reports." Journal of Clinical Psychopharmacology 33, No. 1 (2013): pp. 55-62.
Zwissler, B., et al., "Shaping memory accuracy by left prefrontal transcranial direct current stimulation," The Journal of Neuroscience, 34(11), pp. 4022-4026, 2014.
Office Action for U.S. Appl. No. 14/987,467, dated Jan. 17, 2017.
Response to Office Action for U.S. Appl. No. 14/987,467, dated Mar. 14, 2017.
John R Anderson, John F Anderson, Jennifer L Ferris, Jon M Fincham, and Kwan-Jin Jung. Lateral inferior prefrontal cortex and anterior cingulate cortex are engaged at different stages in the solution of insight problems. Proceedings of the National Academy of Sciences, 106(26): pp. 10799-10804, 2009.
Andrea Antal and Walter Paulus. Transcranial direct current stimulation and visual perception. Perception, 37(3): pp. 367-374, 2008.
Angelakis Efthymios, Stamatina Stathopoulou, Jennifer L. Frymiare, Deborah L. Green, Joel F. Lubar, and John Kounios. "EEG neurofeedback: a brief overview and an example of peak alpha frequency training for cognitive enhancement in the elderly." The Clinical Neuropsychologist 21, No. 1 (2007): pp. 110-129.
Hasan Ayaz, MP Cakir, K Izzetoglu, Adrian Curtin, Patricia A Shewokis, Scott C Bunce, and Banu Onaral. Monitoring expertise development during simulated uav piloting tasks using optical brain imaging. In Aerospace Conference, 2012 IEEE, pp. 1-11. IEEE, 2012.
Hasan Ayaz, Patricia A Shewokis, Scott Bunce, Kurtulus Izzetoglu, Ben Willems, and Banu Onaral. Optical brain monitoring for operator training and mental workload assessment. Neuroimage, 59(1): pp. 36-47, 2012.
Hasan Ayaz, Ben Willems, B Bunce, Patricia A Shewokis, Kurtulus Izzetoglu, Sehchang Hah, A Deshmukh, and Banu Onaral. Cognitive workload assessment of air traffic controllers using optical brain imaging sensors. Advances in understanding human performance: neuroergonomics, human factors design, and special populations, pp. 21-31, 2010.
Richard P Chi and Allan W Snyder. Facilitate insight by non-invasive brain stimulation. PLoS One, 6(2): pp. e16655-1 through 7, 2011.
Evangelia G Chrysikou, Roy H Hamilton, H Branch Coslett, Abhishek Datta, Marom Bikson, and Sharon L Thompson-Schill. Noninvasive transcranial direct current stimulation over the left prefrontal cortex facilitates cognitive flexibility in tool use. Cognitive Neuroscience, (ahead-of-print): pp. 1-9, 2013.
Dylan Edwards, Mar Cortes, Abhishek Datta, Preet Minhas, Eric M Wassermann, and Marom Bikson. Physiological and modeling evidence for focal transcranial electrical brain stimulation in humans: a basis for high-definition tdcs. NeuroImage, 2013, pp. 266-275.
Felipe Fregni, Paulo S Boggio, Michael Nitsche, Felix Bermpohl, Andrea Antal, Eva Feredoes, Marco A Marcolin, Sergio P Rigonatti, Maria TA Silva, Walter Paulus, et al. Anodal transcranial direct current stimulation of prefrontal cortex enhances working memory. Experimental Brain Research, 166(1): pp. 23-30, 2005.

Theodore J Huppert, Solomon G Diamond, Maria A Franceschini, and David A Boas. Homer: a review of time-series analysis methods for near-infrared spectroscopy of the brain. Applied optics, 48(10): pp. D280-D298, 2009.
Arns Martijn, Sabine de Ridder, Ute Strehl, Marinus Breteler, and Anton Coenen. "Efficacy of neurofeedback treatment in ADHD: the effects on inattention, impulsivity and hyperactivity: a meta-analysis." Clinical EEG and neuroscience 40, No. 3 (2009): pp. 180-189.
Meltem Izzetoglu, Kurtulus Izzetoglu, Scott Bunce, Hasan Ayaz, Ajit Devaraj, Banu Onaral, and Kambiz Pourrezaei. Functional near-infrared neuroimaging. Neural Systems and Rehabilitation Engineering, IEEE Transactions on, 13(2): pp. 153-159, 2005.
Satoru Kohno, Ichiro Miyai, Akitoshi Seiyama, Ichiro Oda, Akihiro Ishikawa, Shoichi Tsuneishi, Takashi Amita, and Koji Shimizu. Removal of the skin blood flow artifact in functional near-infrared spectroscopic imaging data through independent component analysis. Journal of biomedical optics, 12(6): pp. 062111-1-062111-9, 2007.
John Kounios and Mark Beeman. The Aha! moment: The cognitive neuroscience of insight. Current Directions in Psychological Science, 18(4): pp. 210-216, 2009.
John Kounios and Mark Beeman. The cognitive neuroscience of insight. Annual Review of Psychology, 65(1), 2013, pp. 71-93.
John Kounios, Jessica I Fleck, Deborah L Green, Lisa Payne, Jennifer L Stevenson, Edward M Bowden, and Mark Jung-Beeman. The origins of insight in resting-state brain activity. Neuropsychologia, 46(1): pp. 281-291, 2008.
John Kounios, Jennifer L Frymiare, Edward M Bowden, Jessica I Fleck, Karuna Subramaniam, Todd B Parrish, and Mark Jung-Beeman. The prepared mind neural activity prior to problem presentation predicts subsequent solution by sudden insight. Psychological Science, 17(10): pp. 882-890, 2006.
Merzagora, Anna C., G. Foffani, I. Panyavin, L. Mordillo-Mateos, J. Aguilar, Banu Onaral, and A. Oliviero. "Prefrontal hemodynamic changes produced by anodal direct current stimulation." Neuroimage 49, No. 3 (2010): pp. 2304-2310.
Nili Metuki, Tal Sela, and Michal Lavidor. Enhancing cognitive control components of insight problems solving by anodal tdcs of the left dorsolateral prefrontal cortex. Brain Stimulation, 5(2): pp. 110-115, 2012.
R Sparing, M Thimm, MD Hesse, J Mist, H Karbe, and GR Fink. Bidirectional alterations of interhemispheric parietal balance by non-invasive cortical stimulation. Brain, 132(11): pp. 3011-3020, 2009.
Izzetoglu, K., Ayaz, H., Hing, J., Shewokis, P., Bunce, S., Oh, P., and Onaral, B. (2014). "UAV Operators Workload Assessment by Optical Brain Imaging Technology (fNIR)," in Handbook of Unmanned Aerial Vehicles, eds. K.P. Valavanis & G.J. Vachtsevanos. Springer Netherlands), pp. 2475-2500.
Roy, D., Sigala, R., Breakspear, M., McIntosh, A. R., Jirsa, V. K., Deco, G., & Ritter, P. (2014). Using the virtual brain to reveal the role of oscillations and plasticity in shaping brain's dynamical landscape. Brain connectivity, 4(10), pp. 791-811.
Merzagora, A.C., G. Foffani, I. Panyavin, L. Mordillo-Mateos, J. Aguilar, Banu Onaral, and A. Oliviero. "Prefrontal hemodynamic changes produced by anodal direct current stimulation." Neuroimage 49, No. 3 (2010): pp. 2304-2310.
Bikson, M., Rahman, A., & Datta, A. (2012). "Computational models of transcranial direct current stimulation." Clinical EEG and Neuroscience, 43(3), pp. 176-183.
Molaee-Ardekani, B., et al., (Available on line 2012). "Effects of transcranial Direct Current Stimulation (tDCS) on cortical activity: A computational modeling study." Brain Stimulation, 6, (2013), pp. 25-39.
Norman, K. A., & O'Reilly, R. C. (2003). "Modeling hippocampal and neocortical contributions to recognition memory: a aomplementary-learning-systems approach." Psychological review, 2003, vol. 110, No. 4, pp. 611-646.
John R Anderson, Daniel Bothell, Michael D Byrne, Scott Douglass, Christian Lebiere, and Yulin Qin. "An integrated theory of the mind." Psychological review, 2004, vol. 111, No. 4, pp. 1036-1060.

(56) References Cited

OTHER PUBLICATIONS

Andrea Antal and Walter Paulus. "Transcranial direct current stimulation and visual perception." Perception, 37(3): pp. 367-374, 2008.
Hasan Ayaz, MP Cakir, K Izzetoglu, Adrian Curtin, Patricia A Shewokis, Scott C Bunce, and Banu Onaral. "Monitoring expertise development during simulated uav piloting tasks using optical brain imaging." In Aerospace Conference, 2012 IEEE, pp. 1-11. IEEE, 2012.
Siwei Bai, Colleen Loo, and Socrates Dokos. A review of computational models of transcranial electrical stimulation. Critical Reviews™ in Biomedical Engineering, 41(1): pp. 21-35 (2013).
Paulo S Boggio, Roberta Ferrucci, Sergio P Rigonatti, Priscila Covre, Michael Nitsche, Alvaro Pascual-Leone, and Felipe Fregni. "Effects of transcranial direct current stimulation on working memory in patients with parkinson's disease." Journal of the neurological sciences, 249(1): pp. 31-38, 2006.
Jeffrey J Borckardt, M. Bikson, H. Frohman, S. T Reeves, A. Datta, V. Bansal, A. Madan, K. Barth, and M. S George. "A pilot study of the tolerability and effects of high-definition transcranial direct current stimulation (hd-tdcs) on pain perception." The Journal of Pain, 13(2): pp. 112-120, 2012.
Jelmer P Borst and John R Anderson. "Using model-based functional mri to locate working memory updates and declarative memory retrievals in the fronto-parietal network." Proceedings of the National Academy of Sciences, 110 (5): pp. 1628-1633, 2013.
Angela Brunstein, Shawn Betts, and John R Anderson. "Practice enables successful learning under minimal guidance." Journal of Educational Psychology, 2009, vol. 101, No. 4, pp. 790-802.
Richard P Chi and Allan W Snyder. "Facilitate insight by non-invasive brain stimulation." PLoS One, 6(2):e16655, 2011, pp. 1-7.
Evangelia G Chrysikou, Roy H Hamilton, H Branch Coslett, Abhishek Datta, Marom Bikson, and Sharon L Thompson-Schill. "Noninvasive transcranial direct current stimulation over the left prefrontal cortex facilitates cognitive flexibility in tool use." Cognitive Neuroscience, (ahead-of-print): pp. 1-9, 2013.
Larry 7 Daily, Marsha C Lovell, and Lynne M Reder. "Modeling individual differences in working memory performance: A source activation account." Cognitive Science, 25(3): pp. 315-353, 2001.
Abhishek Datta, Varun Bansal, Julian Diaz, Jinal Patel, Davide Reato, and Marom Bikson. "Gyri-precise head model of transcranial direct current stimulation: improved spatial focality using a ring electrode versus conventional rectangular pad." Brain stimulation, 2(4): pp. 201-207, 2009.
Abhishek Datta, Dennis Truong, Preet Minhas, Lucas C Parra, and Marom Bikson. "Inter-individual variation during transcranial direct current stimulation and normalization of dose using mri-derived computational models." Frontiers in Psychiatry, Neuropsychiatric Imagining and Stimulation, Oct. 2012, vol. 3, Article 91, pp. 1-8.
A. Datta, M. Elwassif, F. Battaglia, and M. Bikson, "Transcranial current stimulation focality using disc and ring electrode configurations: Fem analysis," J Neural Eng, vol. 5, pp. 163-174, 2008.
Eran Dayan, Nitzan Censor, Ethan R Buch, Marco Sandrini, and Leonardo G Cohen. "Noninvasive brain stimulation: from physiology to network dynamics and back." Nature neuroscience, 16(7): pp. 838-844, 2013.
Mario Dipoppa and Boris S Gutkin. "Flexible frequency control of cortical oscillations enables computations required for working memory." Proceedings of the National Academy of Sciences, (PNAS) Jul. 30, 2013, vol. 110, No. 31, pp. 12828-12833.
Jacek P Dmochowski, Abhishek Datta, Marom Bikson, Yuzhuo Su, and Lucas C Parra. "Optimized multi-electrode stimulation increases focality and intensity at target." Journal of neural engineering, 8(4):046011 (16pp), 2011.
Colleen A Dockery, Ruth Hueckel-Weng, Niels Birbaumer, and Christian Plewnia. "Enhancement of planning ability by transcranial direct current stimulation." The Journal of Neuroscience, 29(22): pp. 7271-7277, 2009.
Dylan Edwards, Mar Cortes, Abhishek Datta, Preet Minhas, Eric M Wassermann, and Marom Bikson. "Physiological and modeling evidence for focal transcranial electrical brain stimulation in humans: a basis for high-definition tdcs." NeuroImage 74 (2013) pp. 266-275.
Brian Falcone, Brian A Coffman, Vincent P Clark, and Raja Parasuraman. Transcranial direct current stimulation augments perceptual sensitivity and 24-hour retention in a complex threat detection task. PloS one, 7(4): 34993, 2012, pp. 1-10.
Felipe Fregni, Paulo S Boggio, Michael Nitsche, Felix Bermpohl, Andrea Antal, Eva Feredoes, Marco A Marcolin, Sergio P Rigonatti, Maria TA Silva, Walter Paulus, et al. "Anodal transcranial direct current stimulation of prefrontal cortex enhances working memory." Experimental Brain Research, 166(1): pp. 23-30, 2005.
Tobias U Hauser, Stephanie Rotzer, Roland H Grabner, Susan Merillat, and Lutz Jäncke. "Enhancing performance in numerical magnitude processing and mental arithmetic using transcranial direct current stimulation (tdcs)." Frontiers in iuman neuroscience, Jun. 2013, vol. 7, Article 244, pp. 1-9.
Theodore J Huppert, Solomon G Diamond, Maria A Franceschini, and David A Boas. "Homer: a review of time-series analysis methods for near-infrared spectroscopy of the brain." Applied Optics, vol. 48, No. 10, Apr. 2009, pp. D280-D298.
Meltem Izzetoglu, Kurtulus Izzetoglu, Scott Bunce, Hasan Ayaz, Ajit Devaraj, Banu Onaral, and Kambiz Pourrezaei. "Functional near-infrared neuroimaging. Neural Systems and Rehabilitation Engineering," IEEE Transactions on, 13(2): pp. 153-159, 2005.
Susanne M Jaeggi, Martin Buschkuehl, John Jonides, and Walter J Perrig. "Improving fluid intelligence with training on working memory." Proceedings of the National Academy of Sciences, 105(19): pp. 6829-6833, 2008.
Mark Jung-Beeman, Edward M Bowden, Jason Haberman, Jennifer L Frymiare, Stella Arambel-Liu, Richard Greenblatt, Paul J Reber, and John Kounios. "Neural activity when people solve verbal problems with insight." PLoS biology, Apr. 2004, vol. 2, Issue 4, pp. 0500-0510.
Juvina, Ion, Tiffany S. Jastrzembski, and R. A. McKinley. "When to apply brain stimulation to achieve learning acceleration." In Proceedings of the International Conference on Cognitive Modeling (ICCM), pp. 358-363. 2013.
Khedr, et al., "Effect of Anodal Versus Cathodal Transcranial Direct Current Stimulation on Stroke Rehabilitation: A Pilot Randomized Controlled Trial", Neurorehabil Neural Repair, 27: pp. 592-601, 2013.
Satoru Kohno, Ichiro Miyai, Akitoshi Seiyama, Ichiro Oda, Akihiro Ishikawa, Shoichi Tsuneishi, Takashi Amita, and Koji Shimizu. "Removal of the skin blood flow artifact in functional near-infrared spectroscopic imaging data through independent component analysis." Journal of biomedical optics, 12(6): pp. 062111-1-062111-9, 2007.
John Kounios and Mark Beeman. "The cognitive neuroscience of insight." Annual Review of Psychology, 65(1), 2013, pp. 71-93.
John Kounios, Jessica I Fleck, Deborah L Green, Lisa Payne, Jennifer L Stevenson, Edward M Bowden, and Mark Jung-Beeman. "The origins of insight in resting-state brain activity." Neuropsychologia, 46(1): pp. 281-291, 2008.
John Kounios, Jennifer L Frymiare, Edward M Bowden, Jessica I Fleck, Karuna Subramaniam, Todd B Parrish, and Mark Jung-Beeman. "The prepared mind neural activity prior to problem presentation predicts subsequent solution by sudden insight." Psychological Science, 17(10): pp. 882-890, 2006.
Hsiao-I Kuo, Marom Bikson, Abhishek Datta, Preet Minhas, Walter Paulus, Min-Fang Kuo, and Michael A Nitsche. "Comparing cortical plasticity induced by conventional and high-definition 4×1 ring tdcs: a neurophysiological study." Brain Stimulation, 6, (2013), pp. 644-648, (Available online Nov. 11, 2012).
Lebiere, Christian, Peter Pirolli, Robert Thomson, Jaehyon Paik, Matthew Rutledge-Taylor, James Staszewski, and John R. Anderson. "A functional model of sensemaking in a neurocognitive architecture." Computational intelligence and neuroscience, vol. 2013, (2013): Article No. 5, pp. 1-59.
Stéphanie Lefebvre, Patrice Laloux, André Peeters, Philippe Desfontaines, Jacques Jamart, and Yves Vandermeeren. "Dual-tdcs enhances online motor skill learning and long-term retention in

(56) References Cited

OTHER PUBLICATIONS chronic stroke patients." Frontiers in human neuroscience, Jan. 2013, vol. 6, Article 343, pp. 1-17, (Available on line 2012).

Lehman, Jill Fain, John Laird, and Paul Rosenbloom. "A Gentle Introduction to Soar, an Architecture for Human Cognition: 2006 Update." University of Michigan (2006), pp. 1-37.

Jorge Leite, Sandra Carvalho, Felipe Fregni, and Oscar F Gonġalves. "Task-specific effects of tdcs-induced cortical excitability changes on cognitive and motor sequence set shifting performance." PloS one, Sep. 2011, vol. 6, Issue 9, e24140, pp. 1-9.

Paula Sanz Leon, Stuart A Knock, M Marmaduke Woodman, Lia Domide, Jochen Mersmann, Anthony R McIntosh, and Viktor Jirsa. "The Virtual Brain: a simulator of primate brain network dynamics." Frontiers in Neuroinformatics, Jun. 2013, vol. 7, Article 10, pp. 1-23.

Lupyan, G. Mirman, D., Hamilton, R., & Thompson-Schill, S. L. (2012). "Categorization is modulated by transcranial direct current stimulation over left prefrontal cortex." Cognition, 124(1), pp. 36-49.

Oded Meiron and Michal Lavidor. "Prefrontal oscillatory stimulation modulates access to cognitive control references in retrospective metacognitive commentary." Clinical Neurophysiology 125 (2014), pp. 77-82.

Monica Melby-Lervåg and Charles Hulme. "Is working memory training effective? a meta-analytic review." Developmental Psychology, 2013, vol. 49, No. 2, pp. 270-291.

Nili Metuki, Tal Sela, and Michal Lavidor. "Enhancing cognitive control components of insight problems solving by anodal tdcs of the left dorsolateral prefrontal cortex." Brain Stimulation, 5(2): pp. 110-115, 2012.

Earl K Miller and Jonathan D Cohen. "An integrative theory of prefrontal cortex function." Annual review of neuroscience, 24(1): pp. 167-202, 2001.

Behrad Noudoost and Tirin Moore. "Parietal and prefrontal neurons driven to distraction." Nature Neuroscience, 16(1): pp. 8-9, 2013.

N Nozar and S Thompson-Schill. "More attention when speaking: does it help or does it hurt?" Neuropsychologia 51 (2013), pp. 2770-2780.

Cornelia Pirulli, Anna Fertonani, and Carlo Miniussi. "The role of timing in the induction of neuromodulation in perceptual learning by transcranial electric stimulation." Brain Stimulation 6 (2013), pp. 683-689.

\* cited by examiner

| | Behaviors/Process | Results |
|---|---|---|
| Individual Level: An Employee's Contribution to the Team | The employee: cooperates with team members, communicates ideas during meetings, participates in the team's decision-making processes. | The number of ideas contributed by the employee, the turn-around time for the individual's product, the accuracy of data supplied to the team. |
| Team Level: The Team's Performance | The team: runs effective meetings, communicates well as a group, allows all opinions to be heard, comes to consensus on decisions. | Customer satisfaction with the team product, the number of cases the team completed, the cycle time for the team's entire work process. |

(Prior Art)
FIG. 3

Average Data
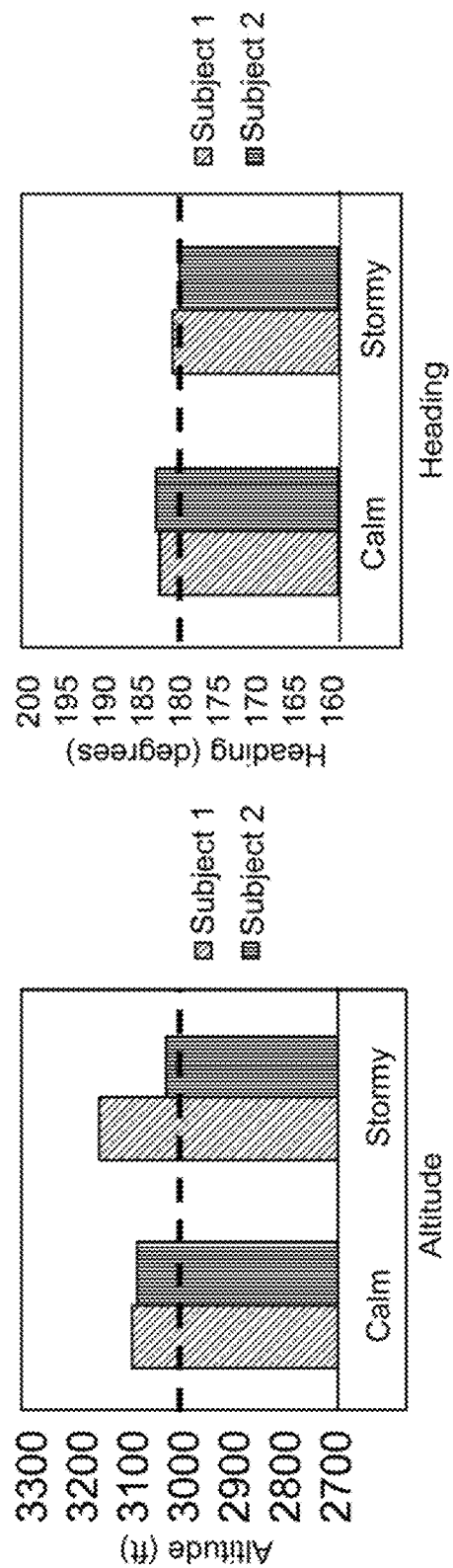
FIG. 7E
FIG. 7F
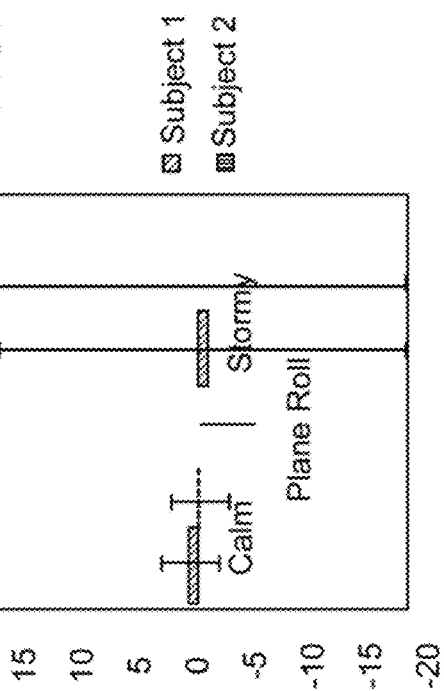
FIG. 7G

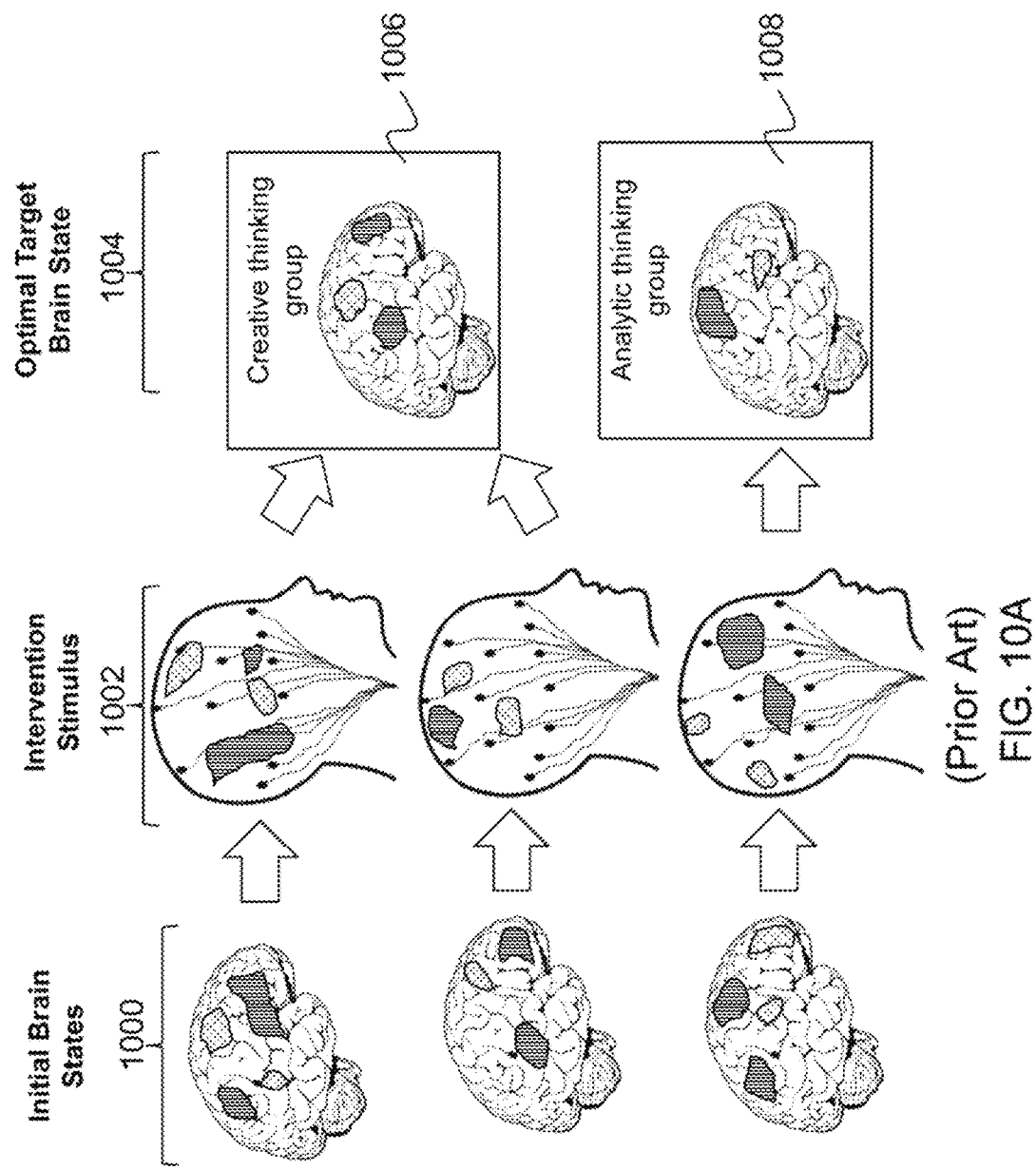

METHOD FOR NEUROSTIMULATION ENHANCED TEAM PERFORMANCE

CROSS-REFERENCE TO RELATED APPLICATIONS

This is a Continuation-in-Part Application of U.S. application Ser. No. 14/987,467, filed in the United States on Jan. 4, 2016, entitled, "The Thinking Cap: Combining Personalized, Model-Driven, and Adaptive High Definition Trans-Cranial Stimulation (HD-tCS) with Functional Near-Infrared Spectroscopy (fNIRS) and Electroencephalography (EEG) Brain State Measurement and Feedback," which is a Non-Provisional Application of U.S. Provisional Application No. 62/099,835, filed in the United States on Jan. 5, 2015, entitled, "The Thinking Cap: Combining Personalized, Model-Driven, and Adaptive HD-tCS with fNIRs and EEG Brain State Measurement and Feedback," the entirety of which are incorporated herein by reference.

This is ALSO a Continuation-in-Part Application of U.S. application Ser. No. 15/219,023, filed in the United States on Jul. 25, 2016, entitled, "System and Methods for Neuro-Playback," which is a Non-Provisional Application of U.S. Provisional Application No. 62/196,155, filed in the United States on Jul. 23, 2015, entitled, "Neuro-Playback," the entirety of which are incorporated herein by reference.

This is ALSO a Non-Provisional Patent Application of U.S. Provisional Application No. 62/210,976 entitled, "A Method for Neurostimulation Enhanced Team Performance" filed in the United States on Aug. 27, 2015, the entirety of which is incorporated herein by reference.

BACKGROUND OF INVENTION

(1) Field of Invention

The present invention relates to a system for enhancing team performance and, more particularly, to a system for enhancing team performance through individualized neurostimulation.

(2) Description of Related Art

Neurostimulation methods have been recently developed as a viable tool for cognitive training and enhancement, rapid recovery from brain injury including stroke, traumatic-brain-injuries, and as a teaching and learning assistance tool. However, while a number of experiments have demonstrated performance enhancement due to various forms of neurostimulation interventions, most studies show high variability and a tendency for some users to do worse even though the overall performance of the user pool improves (see Literature Reference No. 47 in the List of Incorporated Literature References).

Effective team performance depends on strong individual performance, dynamic communication, and adaptation from all members of the team. Research has shown that effective teams require defined and common individual and team goals, trust within the team, clarity in individual roles, open and effective communication, balance in the team's focus, and empowered leaders capable of rapid and effective team management (see Literature Reference Nos. 5, 64, and 65). If any one of these factors break down, poor team performance can result. Research has shown that this problem cannot be remedied with the addition of manpower, but requires well trained individuals capable of adapting their goals to suit the evolving needs of the team in dynamic, confusing and rapidly changing environments and missions (see Literature Reference Nos. 62-65).

Prior work has shown that if two subjects are in communication, common brain activity can be monitored using neuroimaging techniques, such as functional near-infrared spectroscopy (e.g. fNIRS). However, if the listener does not understand or is not paying attention, their measured neural activity does not match the speaker/leaders brain state. These methods are suited to detecting an imbalance in team understanding or communication, but do not take an active role in augmenting individual team member's neural states though feedback or modulation. Additionally, current individual and team training systems rely on live, virtual and constructive training to simulate mission-critical scenarios in order to develop the familiarity and experience of the team.

Current methods of cognitive enhancing neurostimulation have been limited by task specific improvements, a lack of personalization and adaptation, and a limited understanding of mechanistic changes. These methods have shown only limited applicability and transition potential to working environments, as shown in the table of FIG. 3 (from Literature Reference No 64).

Thus, a continuing need exists for a system and method that dynamically stimulates an individual team member's appropriate brain region, allowing the maximal opportunity for focus and understanding of a team leader and mitigation of fatigue.

SUMMARY OF INVENTION

The present invention relates to a system for enhancing team performance and, more particularly, to a system for enhancing team performance through individualized neurostimulation. The system comprises one or more processors and a memory having instructions such that when the instructions are executed, the one or more processors perform multiple operations. A target brain state is selected in a subject, and the target brain state is associated with specific brain regions. A HD-tCS neurostimulation needed to reach the specific brain regions is determined to induce the target brain state in the subject. The determined HD-tCS neurostimulation is applied to the subject while simultaneously sensing, via real-time neuroimaging from both electroencephalography (EEG) and functional near-infrared spectroscopy (fNIRS), neural activity of the subject while the subject performs a behavioral task. Based on the sensed neural activity, the neurostimulation of the subject is adjusted to move the subject into a target brain state.

In another aspect, an assessment of the subject is generated while the subject is performing a behavioral task using neuroimaging data. Any behavioral performance deficiencies in the subject are detected based on the assessment, and behavioral performance deficiencies are associated with activation states in specific brain regions.

In another aspect, a cognitive model for the subject is personalized by: estimating a set of cognitive capacities of the subject from a set of diagnostic tests; mapping the set of cognitive capacities onto a set of parameters; applying the set of parameters to the cognitive model; and predicting the subject's task performance and determining which tasks can be performed to improve the subject's task performance.

In another aspect, the subject's brain state is synchronized with one or more other subjects, allowing all subjects to act in unison when performing tasks.

In another aspect, if the sensed neural activity indicates a loss of focus in the subject, then the HD-tCS neurostimulation is adjusted to reach the specific brain regions needed to regain focus.

In another aspect, the system removes artifacts from a sensed EEG signal using a signal source separation method that uses parallel processing to separate maximally-independent sources of the sensed EEG signal by minimizing mutual information between source data channels.

In another aspect, timing between HD-tCS neurostimulation and sensing via real-time neuroimaging is alternated to avoid interference.

In another aspect, phenotypic subject categories of a target brain state comprise a creative thinking group and an analytic thinking group.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The file of this patent or patent application publication contains at least one drawing executed in color. Copies of this patent or patent application publication with color drawing(s) will be provided by the Office upon request and payment of the necessary fee.

The objects, features and advantages of the present invention will be apparent from the following detailed descriptions of the various aspects of the invention in conjunction with reference to the following drawings, where:

FIG. 3 is a table of team-related measures according to prior art;

FIG. 7E illustrates a comparison of altitude changes for two subjects experiencing calm and stormy flight simulation conditions according to embodiments of the present disclosure;

FIG. 7F illustrates a comparison of heading changes for two subjects experience calm and stormy flight simulation conditions according to embodiments of the present disclosure;

FIG. 7G illustrates a comparison of plane roll changes for two subjects experience calm and stormy flight simulation conditions according to embodiments of the present disclosure;

FIG. 10A illustrates optimal brain state induction for phenotypic subject categories according to prior art;

DETAILED DESCRIPTION

Figure 1:
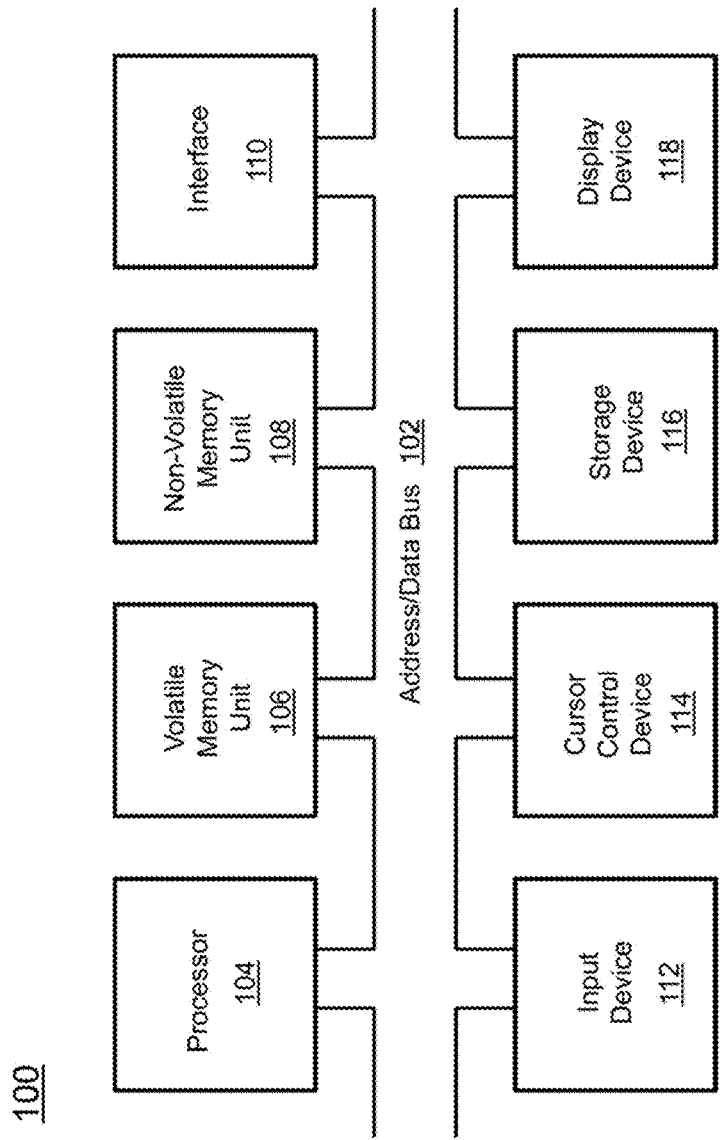
FIG. 1 is a block diagram depicting the components of a system for enhancing team performance according to various embodiments of the present disclosure.

The present invention relates to a system for enhancing team performance and, more particularly, to a system for enhancing team performance through individualized neurostimulation. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

) Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Following that is an introduction that provides an overview of the present invention. Finally, specific details of the present invention are provided to give an understanding of the specific aspects.

(1) List of Incorporated Literature References

The following references are incorporated and cited throughout this application. For clarity and convenience, the references are listed herein as a central resource for the reader. The following references are hereby incorporated by reference as though fully set forth herein. The references are cited in the application by referring to the corresponding literature reference number, as follows:

1. Merzagora, A. C., Foffani, G., Panyavin I., Mordillo-Mateos, L., Aguilar, J., Onaral, B. and A. Oliviero. (2010). Prefrontal hemodynamic changes produced by anodal direct current stimulation. Neuroimage, 49, 3: 2304-2310.
2. Bikson, M., Rahman, A., and Datta, A. (2012). Computational models of transcranial direct current stimulation. Clinical EEG and Neuroscience, 43, 3:176-183.
3. Molaee-Ardekani, B., Márquez-Ruiz, J., Merlet, I., Leal-Campanario, R., Gruart, A., Sánchez-Campusano, R., and Wendling, F. (2012). Effects of transcranial Direct Current Stimulation (tDCS) on cortical activity: A computational modeling study. Brain stimulation.
4. Norman, K. A. and O'Reilly, R. C. (2003). Modeling hippocampal and neocortical contributions to recognition memory: a complementary-learning-systems approach. Psychological review, 110, 4: 611.
5. Anderson, J. R., Bothell, D., Byrne, M. D., Douglass, S., Lebiere, C., and Qin, Y. (2004). An integrated theory of the mind. Psychological review, 111, 4:1036.
6. Antal, A. and Paulus, W. (2008). Transcranial direct current stimulation and visual perception. Perception, 37, 3:367-74.
7. Hasan Ayaz, M. P., Cakir, K., Izzetoglu, Curtin, A., Shewokis, P. A., Bunce S. C., and Onaral, B. (2012). Monitoring expertise development during simulated uav piloting tasks using optical brain imaging. Aerospace Conference. 2012 IEEE, pages 1-11.
8. Siwei, B., Loo, C., and Dokos. S. A review of computational models of transcranial electrical stimulation. (2013). Critical Reviews™ in Biomedical Engineering.
9. Boggio, P. S., Ferrucci, R., Rigonatti, S. P., Covre, P., Nitsche, M., Pascual-Leone, A., and Fregni, F. (2006). Effects of transcranial direct current stimulation on working memory in patients with parkinson's disease. Journal of the neurological sciences, 249, 1:31-38.
10. Borckardt, J. J., Bikson, M., Frohman, H., Reeves, S. T., Datta, A., Bansal, V., Madan, A., Barth, K., and George, M. S. (2012). A pilot study of the tolerability and effects of high-definition transcranial direct current stimulation (hd-tdcs) on pain perception. The Journal of Pain, 13, 2:112-120.
11. Borst, J. P. and Anderson, J. R. (2013). Using model-based functional mri to locate working memory updates and declarative memory retrievals in the fronto-parietal network. Proceedings of the National Academy of Sciences, 110, 5:1628-1633.
12. Brunstein, A., Betts, S., and Anderson, J. A. (2009). Practice enables successful learning under minimal guidance. Journal of Educational Psychology, 101, 4:790.
13. Chi, R. P. and Snyder, A. W. (2011). Facilitate insight by non-invasive brain stimulation. PLoS One, 6, 2:e16655.
14. Chrysikou, E. G., Hamilton, R H., Coslett, H. B., Datta, A., Bikson, M., and Thompson-Schill, S. L. (2013). Noninvasive transcranial direct current stimulation over the left prefrontal cortex facilitates cognitive flexibility in tool use. Cognitive Neuroscience, (ahead-of-print):1-9.
15. Daily, L. Z., Lovett, M. C., and Reder, L. M. (2001). Modeling individual differences in working memory performance: A source activation account. Cognitive Science, 25, 3:315-353.
16. Datta, A., Bansal, V., Diaz, J., Patel, J., Reato, D., and Bikson, M. (2009). Gyri-precise head model of transcranial direct current stimulation: improved spatial focality using a ring electrode versus conventional rectangular pad. Brain stimulation, 2, 4:201-207.
17. Datta, A., Truong, D., Minhas. P., Parra, L. C., and Bikson, M. (2012). Inter-individual variation during transcranial direct current stimulation and normalization of dose using mri-derived computational models. Frontiers in Psychiatry, 3.
18. Dayan, E., Censor, N., Buch, E. R., Sandrini, M., and Cohen, L. G. (2013). Noninvasive brain stimulation: from physiology to network dynamics and back. Nature neuroscience, 16, 7:838-844.
19. Dipoppa, M. and Gutkin, B. S. (2013). Flexible frequency control of cortical oscillations enables computations required for working memory. Proceedings of the National Academy of Sciences.
20. Dmochowski, J. P., Datta, A., Bikson, M., Su, Y., and Parra, L. C. (2011). Optimized multi-electrode stimulation increases focality and intensity at target. Journal of neural engineering, 8, 4:046011.
21. Dockery, C. A., Hueckel-Weng, R., Birbaumer, N., and Plewnia, C. (2009). Enhancement of planning ability by transcranial direct current stimulation. The Journal of Neuroscience, 29, 22:7271-7277.
22. Edwards, D., Cortes, M., Datta, A., Minhas, P., Wassermann, E. M., and Bikson, M. (2013). Physiological and modeling evidence for focal transcranial electrical brain stimulation in humans: a basis for high-definition tdcs. NeuroImage.
23. Falcone, B., Coffman, B. A., Clark, V. P., and Parasuraman, R. (2012). Transcranial direct current stimulation augments perceptual sensitivity and 24-hour retention in a complex threat detection task. PloS one, 7, 4:e34993.
24. Fregni, F., Boggio, P. S., Nitsche, M., Bermpohl, F., Antal, A., Feredoes, E., Marcolin, M. A., Rigonatti, S. P., Silva, M. T. A., Paulus, W., et al. (2005). Anodal transcranial direct current stimulation of prefrontal cortex enhances working memory. Experimental Brain Research, 166, 1:23-30.

25. Hauser, T. U., Rotzer, S., Grabner, R. H., Mérillat, S., and Jäncke, L. (2013). Enhancing performance in numerical magnitude processing and mental arithmetic using transcranial direct current stimulation (tdcs). Frontiers in human neuroscience, 7.
26. Huppert, T. J., Diamond, S. G., Franceschini, M. A., and Boas, D. A. (2009). Homer: a review of time-series analysis methods for near-infrared spectroscopy of the brain. Applied optics, 48, 10:D280-D298.
27. Izzetoglu, M., Izzetoglu, K., Bunce, S., Ayaz, H., Devaraj, A., Onaral, B., and Pourrezaei, K. (2005). Functional near-infrared neuroimaging. Neural Systems and Rehabilitation Engineering, IEEE Transactions on, 13, 2:153-159.
28. Jaeggi, S. M., Buschkuehl, M., Jonides, J., and Perrig, W. J. (2008). Improving fluid intelligence with training on working memory. Proceedings of the National Academy of Sciences, 105, 19:6829-6833.
29. Jung-Beeman, M., Bowden, E. M., Haberman, J., Frymiare, J. L., Arambel-Liu, S., Greenblatt, R., Reber, P. J., and Kounios, J. (2004). Neural activity when people solve verbal problems with insight. PLoS biology, 2, 4:e97.
30. Juvina, I., Jastrzembski, T. S., and McKinley, A. When to apply brain stimulation to achieve learning acceleration.
31. Kohno, S., Miyai, I., Seiyama, A., Oda, I., Ishikawa, A., Tsuneishi, S., Takashi Amita, T., and Shimizu, K. (2007). Removal of the skin blood flow artifact in functional near-infrared spectroscopic imaging data through independent component analysis. Journal of biomedical optics, 12, 6:062111-062111.
32. Kounios, J. and Beeman, M. (2013). The cognitive neuroscience of insight. Annual Review of Psychology, 65, 1.
33. Kounios, J., Fleck, J. I., Green, D. L., Payne, L., Stevenson, J. L., Bowden, E. M., and Jung-Beeman, M. (2008). The origins of insight in resting-state brain activity. Neuropsychologia, 46, 1:281-291.
34. Kounios, J., Frymiare, J. L., Bowden, E. M., Fleck, J. I., Subramaniam, K., Parrish, T. B., and Jung-Beeman, M. (2006). The prepared mind neural activity prior to problem presentation predicts subsequent solution by sudden insight. Psychological Science, 17, 10:882-890.
35. Kuo, H-I., Bikson, M., Datta, A., Minhas, P., Paulus, W., Kuo, M-F., and Nitsche, M. A. (2012). Comparing cortical plasticity induced by conventional and high-definition 4×1 ring tdcs: a neurophysiological study. Brain stimulation.
36. Lebiere, C., Pirolli, P., Thomson, R., Paik, J., Rutledge-Taylor, M., James Staszewski, and Anderson, J. R. (2013). A functional model of sensemaking in a neurocognitive architecture. Computational Intelligence and Neuroscience, 2013:e921695.
37. Lefebvre, S., Laloux, P., Peeters, A., Desfontaines, P., Jamart, J., and Vandermeeren, Y. (2012). Dual-tdcs enhances online motor skill learning and long-term retention in chronic stroke patients. Frontiers in human neuroscience, 6.
38. Lehman, J., Laird, J., and Rosenbloom, P. (2006). A gentle introduction to soar, an architcture for human cognition.
39. Leite, J., Carvalho, S., Fregni, F., and Goncalves, O. F. (2011). Task-specific effects of tdcs-induced cortical excitability changes on cognitive and motor sequence set shifting performance. PloS one, 6, 9:e24140.
40. Leon, P. S., Knock, S. A., Woodman, M. M., Domide, L., Mersmann, J., McIntosh, A. R., and Jirsa, V. (2013). The Virtual Brain: a simulator of primate brain network dynamics. Frontiers in Neuroinformatics, 7.
41. Lupyan, G., Mirman, D., Hamilton, R., & Thompson-Schill, S. L. (2012). Categorization is modulated by transcranial direct current stimulation over left prefrontal cortex. Cognition, 124, 1:36-49.
42. Meiron, O. and Lavidor, M. (2013). Prefrontal oscillatory stimulation modulates access to cognitive control references in retrospective metacognitive commentary. Clinical Neurophysiology.
43. Melby-Lervàg, M. and Hulme, C. (2013). Is working memory training effective? a meta-analytic review. Developmental Psychology, 49, 2:270.
44. Metuki, N., Sela, T., and Lavidor, M. (2012). Enhancing cognitive control components of insight problems solving by anodal tdcs of the left dorsolateral prefrontal cortex. Brain Stimulation, 5, 2:110-115.
45. Miller, E. K. and Cohen, J. D. (2001). An integrative theory of prefrontal cortex function. Annual review of neuroscience, 24, 1:167-202.
46. Noudoost, B. and Moore, T. (2013). Parietal and prefrontal neurons driven to distraction. Nature Neuroscience, 16, 1:8-9.
47. Nozari, N. and Thompson-Schill, S. (2013). More attention when speaking: does it help or does it hurt?
48. Pirulli, C., Fertonani, A., and Miniussi, C. (2013). The role of timing in the induction of neuromodulation in perceptual learning by transcranial electric stimulation. Brain stimulation.
49. Snowball, A., Tachtsidis, I., Popescu, T., Thompson, J., Delazer. M., Zamarian, L., Zhu, T., and Kadosh, R. C. (2013). Long-term enhancement of brain function and cognition using cognitive training and brain stimulation. Current Biology.
50. Soekadar, S. R., Witkowski, M., Cossio, E. G., Birbaumer, N., Robinson, S. E., and Cohen, L. G. (2013). In vivo assessment of human brain oscillations during application of transcranial electric currents. Nature Communications, 4.
51. Sparing, R., Thimm, M., Hesse, M. D., Küst, J., Karbe, H., and Fink, G. R. (2009). Bidirectional alterations of interhemispheric parietal balance by non-invasive cortical stimulation. Brain, 132, 11:3011-3020.
52. Stocco, A. and Anderson, J. R. (2008). Endogenous control and task representation: An fmri study in algebraic problem solving. Journal of Cognitive Neuroscience, 20, 7:1300-1314.
53. Stocco, A., Lebiere, C., and Anderson, J. R. (2010). Conditional routing of information to the cortex: A model of the basal ganglia's role in cognitive coordination. Psychological Review, 117, 2:540-574.
54. Subramaniam, K., Kounios, J., Parrish, T. B., and Jung-Beeman, M. (2009). A brain mechanism for facilitation of insight by positive affect. Journal of Cognitive Neuroscience, 21, 3:415-432.
55. Truong, D. Q., Magerowski, G., Blackburn, G. L., Bikson, and Alonso-Alonso, M. (2013) Computational modeling of transcranial direct current stimulation (tdcs) in obesity: impact of head fat and dose guidelines. NeuroImage: Clinical.
56. Villamar, M. F., Wivatvongvana, P., Patumanond, J., Bikson, M., Truong, D. Q., Datta, A., and Fregni, F. (2013). Focal modulation of the primary motor cortex in fibromyalgia using 4×1-ring high-definition transcranial direct current stimulation (HD-tDCS): immediate and delayed analgesic effects of cathodal and anodal stimulation. The Journal of Pain.
57. Wallach, D. and Lebiere, C. (2003). Conscious and unconscious knowledge: Mapping to the symbolic and subsymbolic levels of a hybrid architecture. In L. Jimenez, editor, Attention and Implicit Learning. John Benjamins, Amsterdam, Netherlands.
58. Javadi, A. H., & Walsh, V. (2012). Transcranial direct current stimulation (tDCS) of the left dorsolateral prefrontal cortex modulates declarative memory. Brain Stimulation, 5(3), 231-241.
59. Patterson, F., Jepson, C., Strasser, A. A., Loughead, J., Perkins, K. A., Gur, R. C., Frey, J. M., Siegel, S., and Lerman, C. (2009). Varenicline improves mood and cognition during smoking abstinence. Biological Psychiatry, 65, 2:144-149.
60. Ahmed, Amir, I A, Ali, A., Kramers, C., Härmark, L., Burger, D. M., and Verhoeven, W. (2013). Neuropsychiatric adverse events of varenicline: a systematic review of published reports. Journal of Clinical Psychopharmacology, 33, 1:55-62.
61. Haddal & Gertler. (2010) Homeland Security: Unmanned Aerial Vehicles and Boarder Surveillance. Congressional Research Service Report for Congress.
62. Attrition: Pilots Despise Flying UAVs. http://www.strategypage.com/htmw/htatrit/articles/20120812.aspx. Taken on Apr. 14, 2016.
63. No One Wants to be a Drone Pilot, U.S. Air Force Discovers. http://w ww.popsci.com/technology/article/2013-08/air-force-drone-program-too-unmanned-its-own-good. Taken on Apr. 14, 2016.
64. Performance Management. http://www.opm.gov/policy-data-oversight/performance-management/reference-materials/historical/facts-about-measuring-team-performance. Taken on Apr. 14, 2016.
65. Konvalinka, I., & Roepstorff, A. (2012). The two-brain approach: how can mutually interacting brains teach us something about social interaction?Frontiers in Human Neuroscience, 6.
66. Bell, Anthony J., and Terrence J. Sejnowski. (1995). "An information-maximization approach to blind separation and blind deconvolution." Neural computation 7, no. 6: 1129-1159.

(2) Principal Aspects

The present invention has three "principal" aspects. The first is a system for enhancing team performance. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, or a field programmable gate array.

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. For example, the input device 112 may include one or more sensors, such as a camera for video or still images, a microphone, or a neural sensor. Other example input devices 112 may include an accelerometer, a GPS sensor, or a gyroscope.

In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
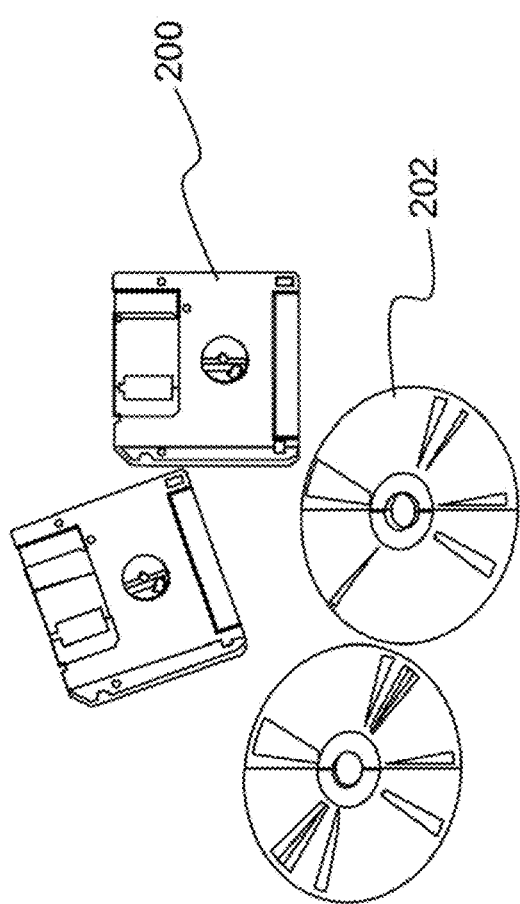
FIG. 2 is an illustration of a computer program product according to various embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Introduction

Effective team performance depends on strong individual performance, dynamic communication, and adaptation from all members of the team. Current individual and team training systems rely on live, virtual and constructive training to simulate mission-critical scenarios in order to develop the familiarity and experience of the team.

The method described in detail below dynamically stimulates the individual team member's appropriate brain region, allowing the maximal opportunity for focus and understanding of the team leaders and the mitigation of fatigue. By monitoring the brain and using individualized neural models to predict the correct team member/leader neural patterns this method can increase the unison within the team leading to greater effectiveness and collaboration between team members.

The system according to embodiments of the present disclosure personalizes and adapts neurostimulation to each team member (FIG. 4) to pinpoint the phenotypic neurobiological mechanisms across a large population with a variety of neural imaging methods. In addition, using the model-driven adaptive performance team system (see, for example, FIG. 5) provides a comprehensive map from team to user to behaviors to brain regions of interest for neurostimulation patterns to enable rapid and specific enhancement of directed cognitive faculties in teams. Other, methods use generic anatomical models (see Literature Reference Nos. 2 and 3) to direct neurostimulation, and cannot make predictions of team or individual behaviors based on neurobiological mechanisms. The present invention provides an elegant system-level solution to several problems in adapting and personalizing neurostimulation for team performance and training.

The system and method described herein addresses these needs by increasing the effectiveness of team performance though model-driven neurostimulation in both operational and training settings though the application of real-time model-driven neurostimulation. Specifically, the system and method described herein allow for the advantageous enhancement of: team communication, objective and goal understanding, increases in goal-directed behavior and adaptability and overall performance. This method not only benefits team performance in mission relevant metrics (i.e., a team may obtained mission objectives faster with less risk to team members and utilizing fewer resources), but it can also mitigate potential accident and injury risks by decreasing fatigue and assisting team members to maintain focus on goals and mission objectives in confusing and challenging real-world scenarios.

Specifically, the method according to various embodiments of the present disclosure has the following advantages over prior work. A combined multimodal neuroimaging and neurostimulation system allows individual team members to act in unison when conducting missions in a controlled environment by synchronizing team members brain states (e.g., amplitude and phase of functional measures of brain states (e.g., EEG frontal synchrony) for mission-critical cognitive functions (i.e., cognitive control allows an individual to ignore distractions and focus on a goal objective).

Additionally, the present invention performs behavioral and neuroimaging monitoring and classification of individual decision making (e.g., with respect to a reference flight path in the pilot training task). Real-time mitigation of fatigue/boredom states via neurostimulation of attentional centers in the brain is used to ultimately decrease an individual's fatigue and improve performance. Behavioral and/or neuroimaging measures show decreased alertness and fatigue, so the system described herein excites the prefrontal cortex to increase arousal in the subject. Continual monitoring of each team member is utilized to ensure focus is kept on the individual objectives, and ensure that team leader and mission instructions and goals are understood and executed to the best of the individual's ability.

Finally, when neuromonitoring signals indicate a loss of focus or understanding, neurostimulation is applied to the correct region of the brain to aid the individual in regaining focus. Increased activity in the neural regions depicted in FIGS. 6A and 6B correspond to focus, attention, and workload. If these appear in the calm condition and behavioral metrics begin to decline (see FIGS. 7A-7G), then the system can infer that the subject is losing focus.

The invention described herein compensates for individual differences using a combination of three innovations that, together, revolutionize the field of neurostimulation. First, the unique high definition (HD) neurostimulation system offers unprecedented specificity and control over the neural activity induced in the brain. Second, a functional-anatomical model, such as The Virtual Brain (see Literature Reference No. 40 for a description of The Virtual Brain), coupled with a cognitive-behavioral model, such as ACT-R (see Literature Reference No. 5 for a description of ACT-R) are adapted to subject performance and brain states. This gives the needed predictive power to personalize both neural stimulation patterns as well as behavioral tasks for maximum adaptive reasoning and problem solving (ARP) enhancement. Third, monitoring brain states during neurostimulation (in addition to before and after) using a combination of neural recordings, including functional near-infrared spectroscopy (fNIRS) and electroencephalography (EEG) offers a deeper understanding of the neural basis for intervention effects, allowing within-trial adaptation of stimuli for improved cognitive flexibility. These innovations ensure that no users degrade in performance. Each of these aspects will be described in further detail below.

(4) Specific Details of the Invention

(4.1) Basic Concept of Operation

Figure 4:
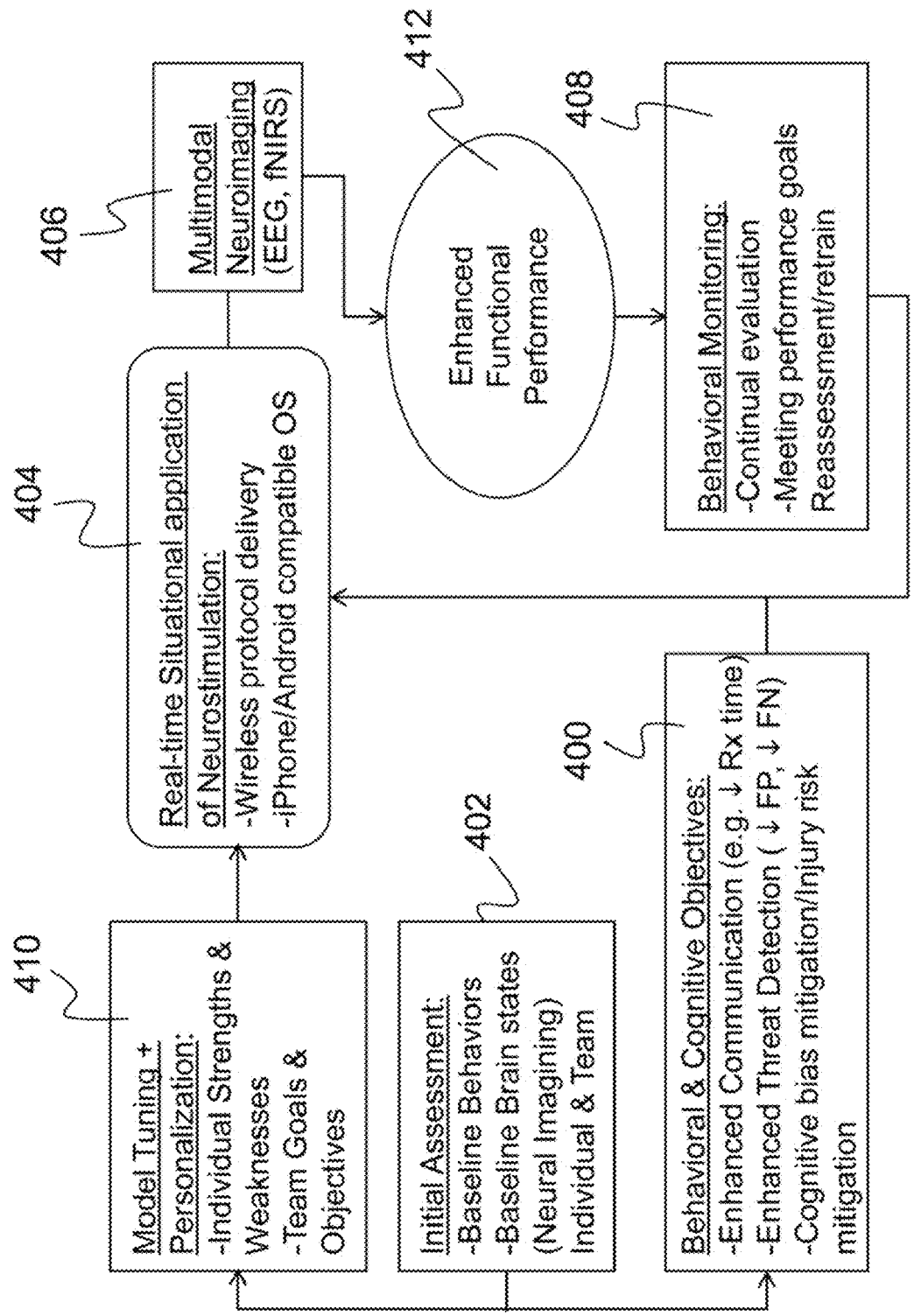
FIG. 4 illustrates a system architecture diagram according to various embodiments of the present disclosure.

The basic concept of operation, shown in FIG. 4, is a multi-step process of choosing the correct behavior and cognitive objectives 400, stimulation location, and parameters for the team member (based on an initial assessment module 402); stimulating the correct brain areas in individual team members (using a real-time situational application of neurostimulation module 404); measuring the changing brain states and behavior (using a multimodal imaging module 406 and a behavioral monitoring module 408); and adapting the team's neurostimulations (using the real-time situational application of neurostimulation module 404). Each team member must be linked to their functional role and goal state requiring specific cognitive faculties (via a model tuning and personalization module 410).

Figure 5:
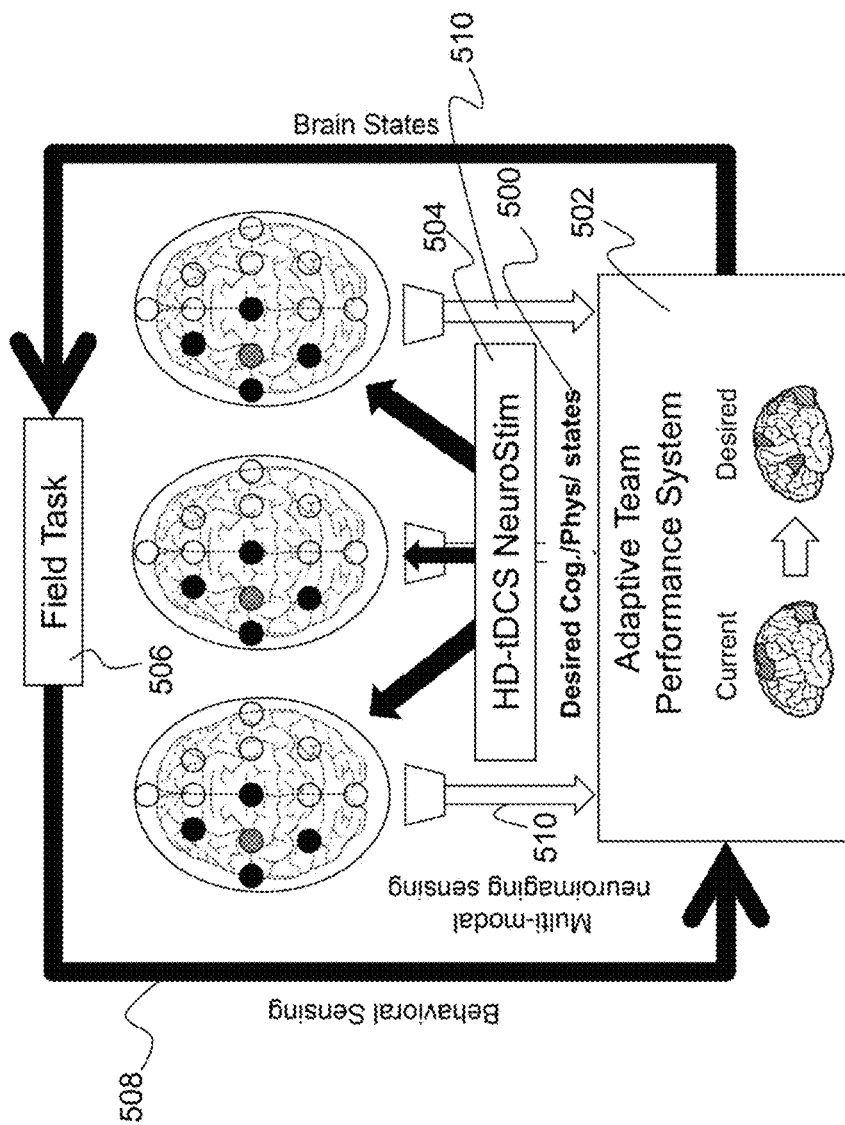
FIG. 5 illustrates model-driven high definition transcranial current stimulation (HD-tCS) for adaptive team performance according to embodiments of the present disclosure.

As depicted in FIG. 5, once the desired cognitive and physical states 500 have been chosen, the adaptive team performance system 502 (comprising a functional-anatomical model and a cognitive-behavior model) will determine what HD-tCS (high definition transcranial current stimulation) neurostimulation 504 will best improve each team member's performance on the specific field task 506.

FIG. 5 illustrates model-driven HD-tCS according to embodiments of the present disclosure which precisely targets each team member's specific brain regions, networks, and dynamic states, with the ability to excite, suppress and synchronize brain regions across team members accurately and adapt in real-time based on behavioral sensing 508 and multi-modal neuroimaging sensing 510.

The functional anatomical model of the adaptive team performance system 502 then determines what stimulation (HD-tCS 504) protocol to use for the given task 506. The first time stimulation occurs, the stimulation will be a general task specific stimulation. The models of the adaptive team performance system 502 will adapt to the personal behavioral responses to the task. As the team member performs tasks, the brain state is measured by multiple neural imaging modalities (e.g., functional near-infrared spectroscopy (fNIRS), electroencephalogram (EEG) and/or functional magnetic resonance imaging (fMRI)), represented by element 510 in FIG. 5 and element 406 in FIG. 4). The behavioral-monitoring module 408 assesses (i.e., behavioral sensing 508) the enhanced functional performance 412 relative to the behavioral and cognitive objectives 400 and recommends modified neurostimulations (elements 404 and 504). Additionally, the behavioral-monitoring module 408 identifies regions of interest to be stimulated which are personalized for the current user based on their target brain state and team performance goal (i.e., model tuning and personalization 410).

(4.2) Multi-Modal Adaptive Mixture Independent Component Analysis (ICA)

The adaptive stimulation approach according to embodiments of the present disclosure incorporates two modes of brain monitoring to facilitate feedback and neurostimulation adaptation for each team member as the intervention takes place. A unique advance was developed to allow both EEG and fNIRS data to be collected during the stimulation intervention. For example, high definition transcranial current stimulation (HD-tCS) electrodes are the same form factor as EEG electrodes and can be placed on the same electrode cap. Interference is avoided between electrical stimulation currents and EEG by alternating the timing of the stimulation and EEG data capture switching up to 250 Hertz (Hz). In this way, snippets of EEG data can be collected throughout the stimulation period without interference.

In multi-modal adaptive mixture independent component analysis the Infomax ICA algorithm achieves minimization of (y) based on the information maximization principle (see Literature Reference No. 66). Extended Infomax is similar to Infomax, with the additional ability to separate mixed non-Gaussian signal distributions. This is done by a learning rule which adaptively changes the sign of the 4th-order moment of the probability density function (PDF) to fit sub- and super-Gaussian distributions. Adaptive Mixture ICA (AMICA) goes a step farther and models adaptive mixtures of Gaussian PDFs fit to individual component time courses and spatial projections in entropy maximization, rather than a selecting single Gaussian or non-Gaussian PDFs.

In the present invention, a multi-modal adaptive-mixture ICA was developed to remove residual artifacts from the EEG signal using a signal source separation method that uses massively parallel processing to separate maximally-independent sources of the EEG signal, by minimizing mutual information between N components, where N is the number of source data channels. The multi-modal adaptive-mixture ICA method was developed to remove 60 Hz line artifacts, eye-blinks, vertical and horizontal eye movements, and cardiac signals (when these signals are present in the data).

The algorithm is a natural gradient descent ICA algorithm (such as Infomax, extended Infomax, and AMICA). This algorithm is an iterative procedure where multiple solutions are examined until a stopping criterion is reached. Entropy (or information content) of the output vectors h(y) is maximized by minimizing the mutual information I(y) shared between them. Entropy h within vector x of random data (e.g., from an EEG sensor) is given by: h(x)=E{−log p(x)}. Entropy h of the vector x is the expected value of the log-transformed PDF for the vector/sensor p(x), which ranges from 0 to 1. In other words, entropy of an EEG channel is the area under the curve of the probability distribution function. Sensor x and component y have a linear relationship by the factor W (y=Wx), and for a linear transformation Y=BX, entropy of the vector Y can be calculated with h(Y)=log |det B|+h(X), so entropy of component y can be calculated with h(y)=log |det W|+h(x). Pairwise, mutual information I between two vectors X1 and X2 (e.g., two EEG sensors or ICA components) can be defined as I(X_1,2)=h(X_1)+h(X_2)−h(X_1,2), or for N components derived from Y sensors I(Y)=h(Y_)+ . . . +h(Y_N)−h(Y). Therefore, mutual information I(y) among component time courses y_(1 . . . n) is given by: I(y)=h (y_1)+ . . . +h(y_n)−log |det W|−h(x).

Figures 6A, 6B:
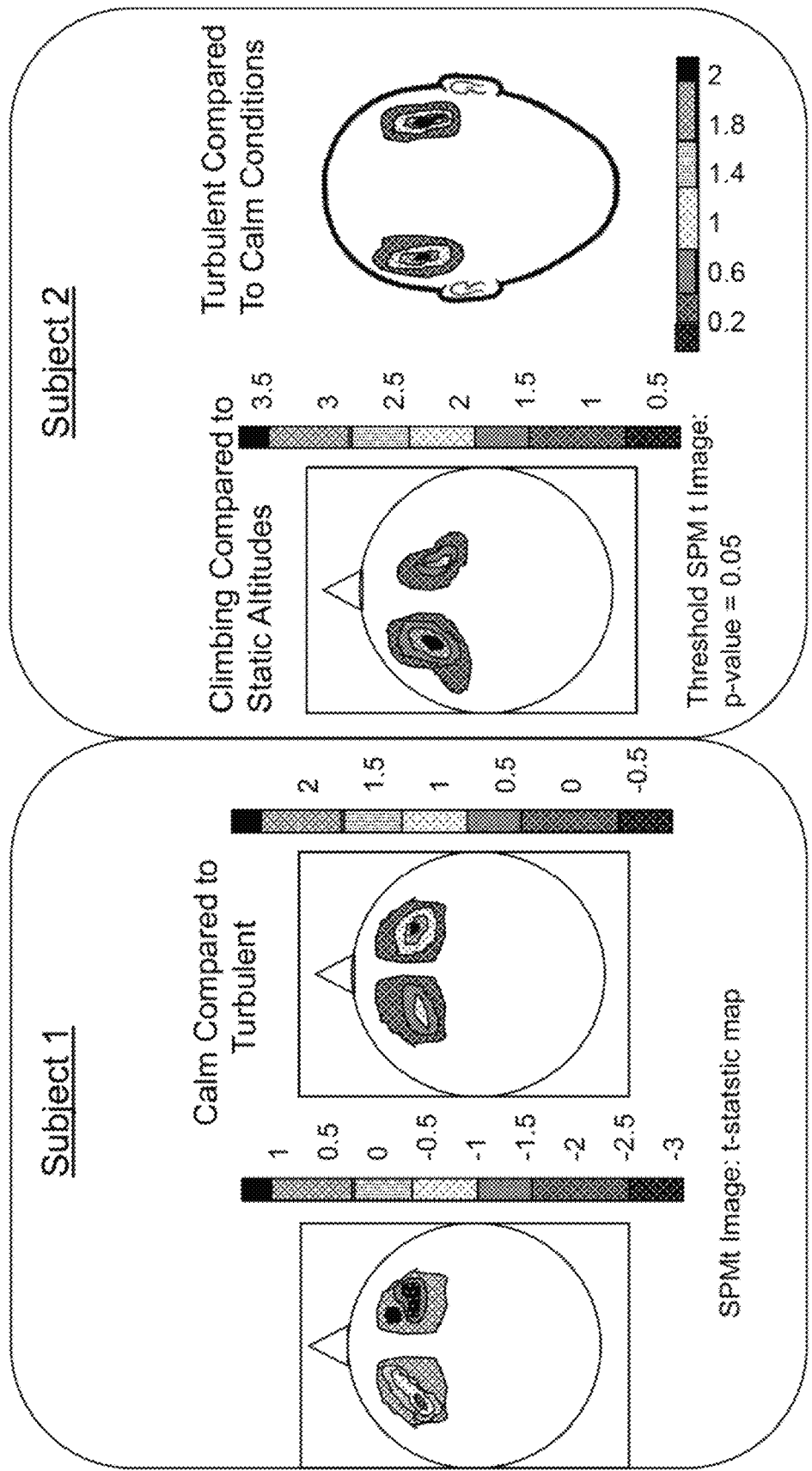
FIG. 6A illustrates hemoglobin concentration differences in subject 1 during climbing compared to level flight, and calm compared to turbulent flight conditions in a simulator according to embodiments of the present disclosure.
FIG. 6B illustrates hemoglobin concentration differences in subject 2 during climbing compared to level flight, and calm compared to turbulent flight conditions in a simulator according to embodiments of the present disclosure.

The system according to various embodiments of the present disclosure uses EEG to monitor dynamic brainwave power in the alpha and gamma frequency bands over the dorsal-lateral pre-frontal cortex (dlPFC) region. This signal is utilized to classify cognitive workload in pilots with one-show classification accuracy of 90%. Functional near-infrared spectroscopy (fNIRS) measures regional activity levels and is used to complement the EEG-based brain state sensing with a mode that has different noise and artifact characteristics, resulting in improved classifier performance when combined with the EEG based sensing. For instance, FIGS. 6A and 6B show fNIRS results of workload classification signals in a calm versus turbulent condition task, which can be used to assess operator vigilance and workload. Prefrontal cortex activity is measured in total hemoglobin (Hb) changes. Thus, FIG. 6A illustrates hemoglobin concentration differences in subject 1 during climbing compared to level flight, and calm compared to turbulent flight conditions. FIG. 6B illustrates hemoglobin concentration differences in subject 2 during climbing compared to level flight, and calm compared to turbulent flight conditions.

The HD-tCS system according to embodiments of the present disclosure supports 9 DC/AC (direct current/alternating current) stimulation channels and 32 EEG channels for concurrent data collection (interleaved up to 250 Hz). The stimulation channels support any combination of three different types of HD-tCS. Direct Current Stimulation (HD-tDCS) is used to inhibit or excite targeted functional brain regions. Alternating Current Stimulation (HD-tACS) induces oscillatory patterns of neural activity with target amplitudes, frequencies, and phases. Random Noise Stimulation (HD-tRNS) will promote neural plasticity. Additional details regarding the different types of HD-tCS can be found in Literature References No. 19, 42, 48, and 49.

(4.3) Behavioral Monitoring and Initial Assessment
(Represented by Elements 408 and 402, Respectively)

Behavioral tasks have been developed to rapidly assess cognitive workload and operator performance in a variety of contexts. The present invention uses performance measures, such as aircraft heading, altitude, roll, pitch, airspeed, and latitude/longitude position to calibrate a pilot's behavioral performance relative to a database of subjects (including commercial and military pilots). These performance metrics are used to calibrate the training and the initial neurostimulation patterns for those subjects, in the team system, these are user-task measures nested into a team performance model. For example, in a simplified navigation and piloting team task, the team's performance metric could be: nav*pilot/(nav+pilot) if nav and pilot scores are 0-1 performance measures.

Figure 7A:
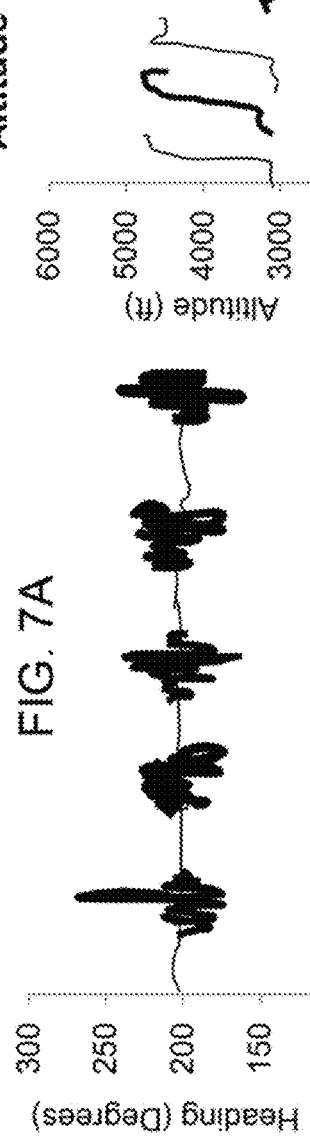
FIG. 7A illustrates changes in heading during stormy and calm simulated flight conditions according to embodiments of the present disclosure.
Figure 7B:
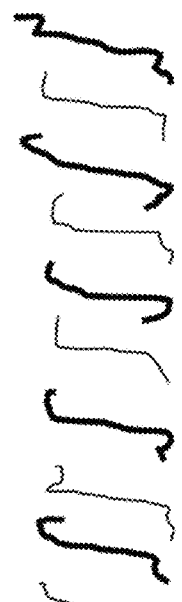
FIG. 7B illustrates changes in altitude during stormy and calm simulated flight conditions according to embodiments of the present disclosure.
Figure 7C:
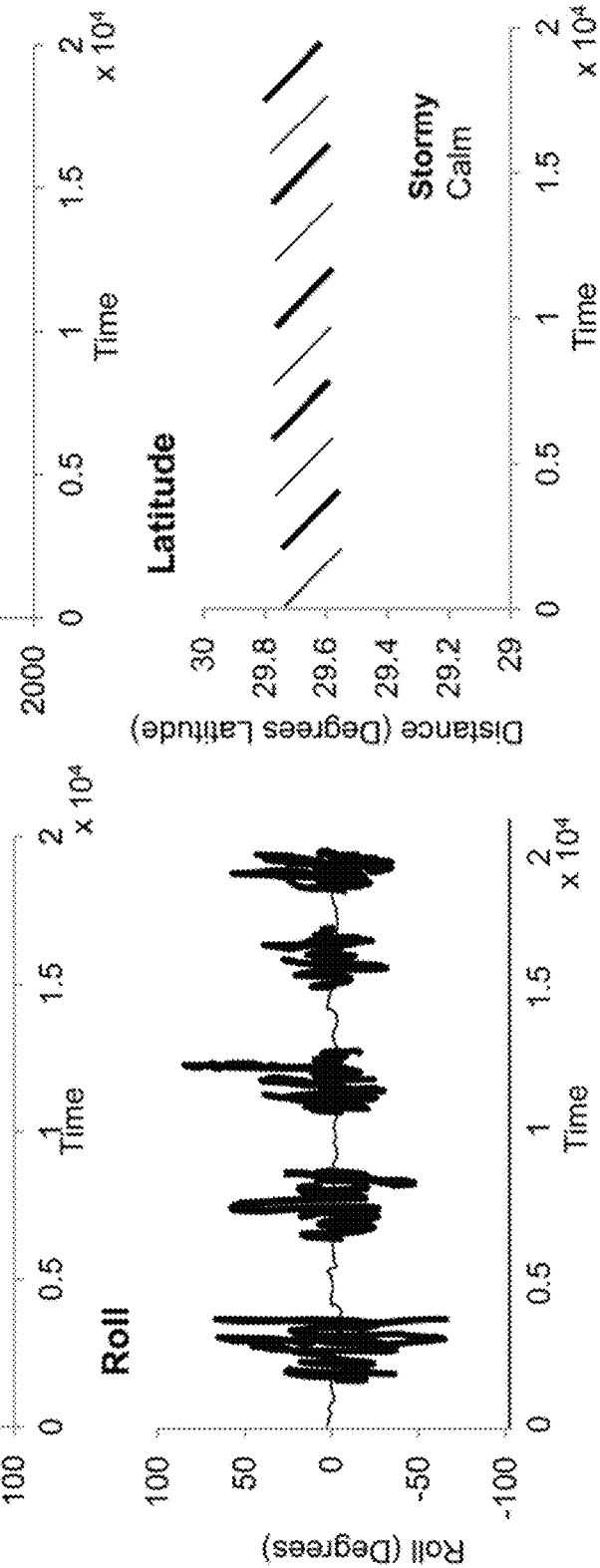
FIG. 7C illustrates changes in plane roll during stormy and calm simulated flight conditions according to embodiments of the present disclosure.
Figure 7D:
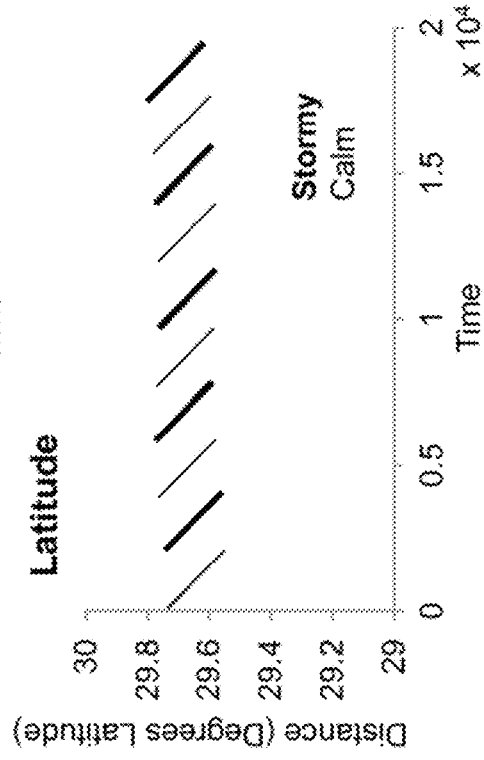
FIG. 7D illustrates changes in latitude during stormy and calm simulated flight conditions according to embodiments of the present disclosure.

FIGS. 7A-7G illustrate pilot behavioral data from two subjects showing behavioral classification of high and low workload conditions during simulated flight. Specifically, FIG. 7A illustrates changes in heading during stormy (high workload, represented by bolded lines) and calm (low workload, represented by unbolded lines) flying conditions. FIG. 7B illustrates changes in altitude during stormy (high workload, represented by bolded lines) and calm (low workload, represented by unbolded lines) flying conditions. FIG. 7C illustrates changes in roll during stormy (high workload, represented by bolded lines) and calm (low workload, represented by unbolded lines) flying conditions. FIG. 7D illustrates changes in latitude during stormy (high workload, represented by bolded lines) and calm (low workload, represented by unbolded lines) flying conditions. FIG. 7E illustrates changes in altitude during stormy and calm flying conditions, comparing two subjects. FIG. 7F illustrates a change in heading during stormy and calm flying conditions, comparing two subjects. FIG. 7G illustrates a change in plane roll during stormy and calm flying conditions, comparing two subjects.

(4.4) Model Tuning and Personalization
(Represented by Element 410)

Individual team-member task strategies and brain states may vary from one person to the next during problem-solving. The system according to various embodiments of the present disclosure has the ability to precisely apply neurostimulation with high resolution to induce personalized brain states for team performance. A generic neurostimulation is inappropriate; therefore, the present invention is model-based, and the models adapt during training from subject-specific fMRI, fNIRS, and EEG data. The behavioral assessment and objectives models (elements 408 and 508) account for individual differences from behavioral and cognitive perspectives and recommend anatomical targets for neurostimulation. These models link to an anatomical model (element 402) to determine a combination of electrode currents to produce on a subject's scalp so as to modulate target brain regions.

The first stage of modeling assesses behavioral performance deficiencies in individual team members and associates them with activation states in various brain regions. To initialize the model, the subject is engaged in a battery of cognitive tasks while scanning with fNIRS and EEG, and the performance is used to parameterize the model. The resulting model can be implemented in a cognitive simulator (such as ACT-R (Adaptive Control of Thought-Rational)). Once parameterized, the model predicts the subject's and team's performance over the full spectrum of related tasks. Using these identified weaknesses, the model will then be used to assemble a set of training tasks. For each task, the model searches for the desired "target" brain states (i.e., the state measured during peak behavioral performance during personalization) that will yield the greatest estimated improvement in overall performance of the team.

The second stage of modeling selects the target brain state in individuals for team performance enhancement. Three-dimensional (3D) Functional-Anatomical models (such as Soterix HDTargets (produced by Soterix Medical, Inc. located at 237 W 35 St., New York, N.Y. 10001) or the Virtual Brain (described in Literature Reference No. 41)) capture both shape and conductance of tissues above and beneath the skull. These models associate functional brain regions for the target brain state to specific physical locations within the skull and provide a means to determine the HD-tCS electrode currents needed to reach these regions effectively. The functional-anatomical model must be initialized from a user's fMRI scan, but during the training regimen it is adapted based on fNIRS sensing, providing a lower-cost rough approximation to fMRI data.

Given a set of brain regions designated for intervention and the desired activations of these regions, the system model (element 502) can derive the needed electrode currents and polarities to induce the target brain state (see Literature Reference No. 40. The stimulation is applied while the subject is engaged in the selected task. Finally, the HD-tCS currents guide subjects' neural activity during the tasks into states that assist subjects in realizing peak team performance. These target brain states promote neural plasticity essential for improvement and persistence, while also enhancing the generalizability and retention of the cognitive skills developed during the training (described in Literature Reference Nos. 23, 25, and 37.

(4.4.1) Model Personalization

Personalization consists of two main approaches: setting architectural parameters (described in Literature Reference No. 15) and defining knowledge and skill structures (described in Literature Reference No. 57). In the first approach, cognitive capacities of each team member are estimated from diagnostic tests (e.g., working memory capacity, set-shifting ability, reaction times, recall accuracy) and are then mapped onto architectural parameters based on the range of skill within a population (e.g., 1-poor, 10-best). These parameters are then applied to the cognitive model to predict an individual's task performance and determine which tasks (and stimulations) will show the most generalized improvements of the individual and the team. The latter approach to personalization is to estimate the state of an individual's knowledge from the subject's performance (e.g., intelligent tutoring) and to determine which knowledge structures (e.g., hippocampal system for memory performance, pre-frontal cortex working memory capacity, executive function) the participant has available and which new structures (e.g., skills) would maximize the team's task performance. Intelligent tutoring systems, such as ACT-R, can estimate the state of an individual's skill or knowledge based on their behavior.

(4.5) Real-Time Neurostimulation Application (Represented by Element 404)

Another element of the method according to some embodiments of the present disclosure is to dynamically alter the stimulus currents based on sensor feedback of the team's brain states both before and during engagement in behavioral tasks. Some embodiments may be utilized to manipulate the oscillatory dynamics present in neural activity of specific brain regions in order to train and assist team members in flexibly switching between operational modes (e.g., synchronized (dissemination of knowledge/tasks to subordinates as in FIG. 9B), and unsynchronized (each team member is performing independently on their separate tasks). The method described herein functions by incorporating alternating current stimulation (HD-tACS), at gamma-band frequencies (~40 Hz), for activation and alpha-band frequencies (~10 Hz) for suppression into a feedback loop that involves real-time sensing from both EEG and fNIRS. Data from both modalities is used during the course of transcranial team stimulation.

In order to solve complex real-world problems, teams need to be adaptive and use a combination of problem-solving strategies, as described in Literature Reference No. 32. However, most team members tend to have a natural predilection toward using one strategy or the other (described in Literature Reference No. 33), and they have difficulty switching between them. Recent neuroimaging research has identified differences in brain states associated with analysis and insight (see Literature Reference No. 32). For example, insight solving involves a burst of activity in the right temporal lobe (see Literature Reference No. 29). Immediately prior to the presentation of an expected problem, subsequent insight solving is associated with elevated activity in the anterior cingulate and bilateral temporal lobes (see Literature Reference No. 34).

The real-time, closed-loop, multi-modal sensing and adaptive-mixture ICA according to embodiments of the present disclosure informs the behavioral and functional models for guided, adaptive and personalized team neurostimulation to steer each member toward their desired brain states. There are two key benefits of this capability. First, it increases the efficiency and efficacy of traditional neurostimulation and neurofeedback training in which a team member will learn to "mentally steer" his or her brain state towards one of two target states. Second, it allows the induction of the desired target brain states while a user is actively engaged in behavior, a capability that is infeasible during traditional neurofeedback training.

The unique method of adaptive stimulation described herein facilitates a more flexible switching between modes of problem solving. For example, the method according to embodiments of the present disclosure can induce the analytic brain state in subjects by stimulating their anterior cingulate region with alpha frequencies to decrease activity (see Literature Reference No. 50 for a description of inducing the analytic brain state). This reduces the brain's monitoring of competing solution possibilities, resulting in a focused analytic strategy that follows the dominant, obvious, path to solution (see Literature Reference Nos. 34 and 54). As cognitive workload increases, presumably because the user is stuck and can't make further progress, the system guides the user to enter the insight brain state and then resume the task. This involves the cognitive-behavioral and functional-anatomical models stimulating the anterior cingulate region with gamma frequencies to increase activity. This operation sensitizes users to competing, nonobvious solution possibilities, or "long shot" ideas. When the anterior cingulate detects weak, unconscious ideas, it can signal dorsolateral PFC to switch to one (as described in Literature Reference No. 45), resulting in an insight, as described in Literature Reference No. 29. Weak, unconscious ideas are detected based on a comparison between the current and a salient template to signal the PFC.

Figure 8A:
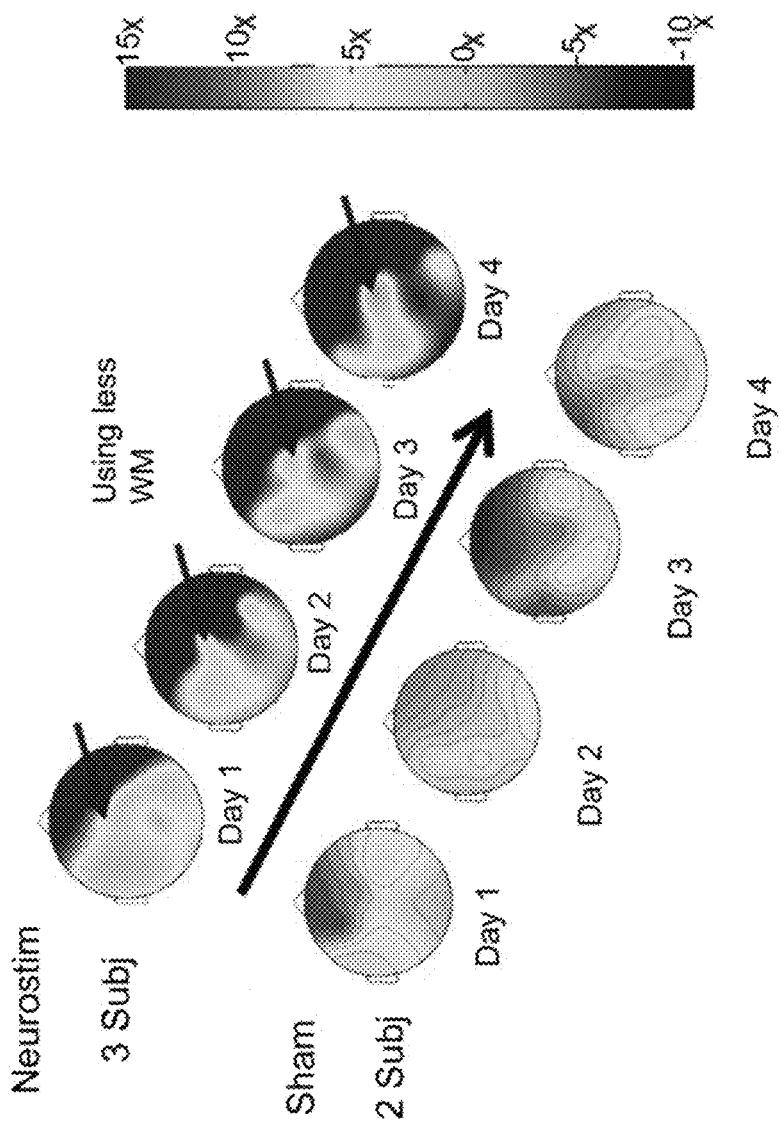
FIG. 8A illustrates changes in electroencephalogram (EEG) patterns across four consecutive days of flight training according to embodiments of the present disclosure.
Figure 8B:
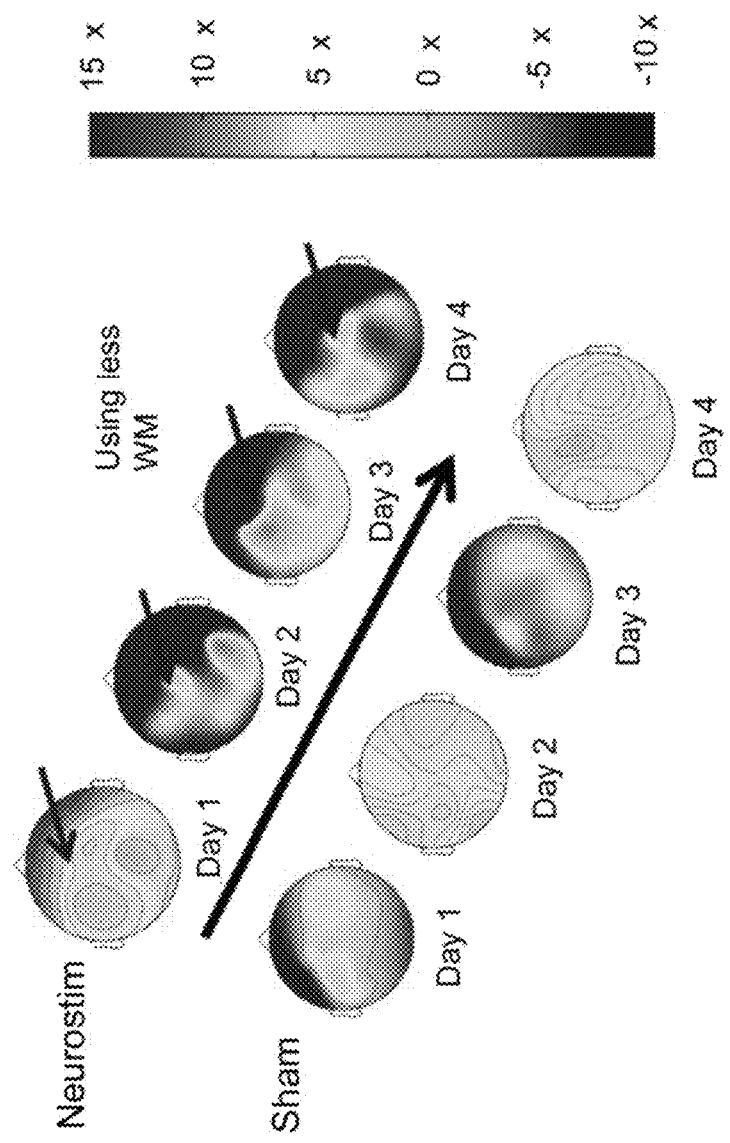
FIG. 8B illustrates changes in EEG patterns across four consecutive days of flight training during a working memory task according to embodiments of the present disclosure.
Figures 9A, 9B:
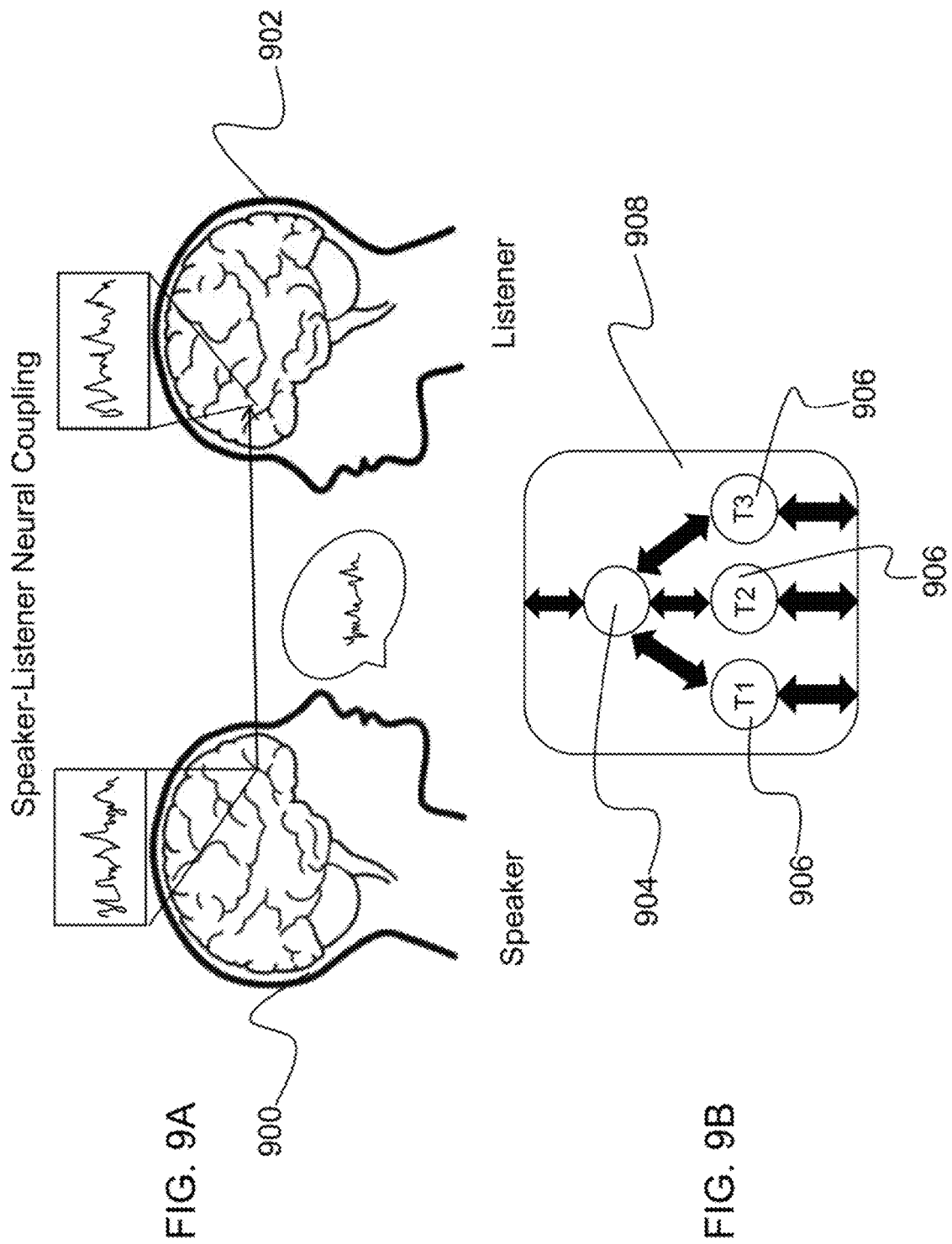
FIG. 9A illustrates speaker-listener neural coupling according to embodiments of the present disclosure.
FIG. 9B illustrates how a team leader defers tasks to subordinate members in a hierarchical team structure according to embodiments of the present disclosure.

FIGS. 8A and 8B show the changes in EEG patterns of groups (neurostimulation and sham/control) across four consecutive days of flight training (FIG. 8A) and during a work memory task (FIG. 8B). FIG. 9A depicts the neural synchrony between speaker 900 and listener 902 teams. FIG. 9B illustrates how a team leader 904 defers tasks to subordinate members (T1-T3) 906 in a hierarchical team structure 908.

Figure 10B:
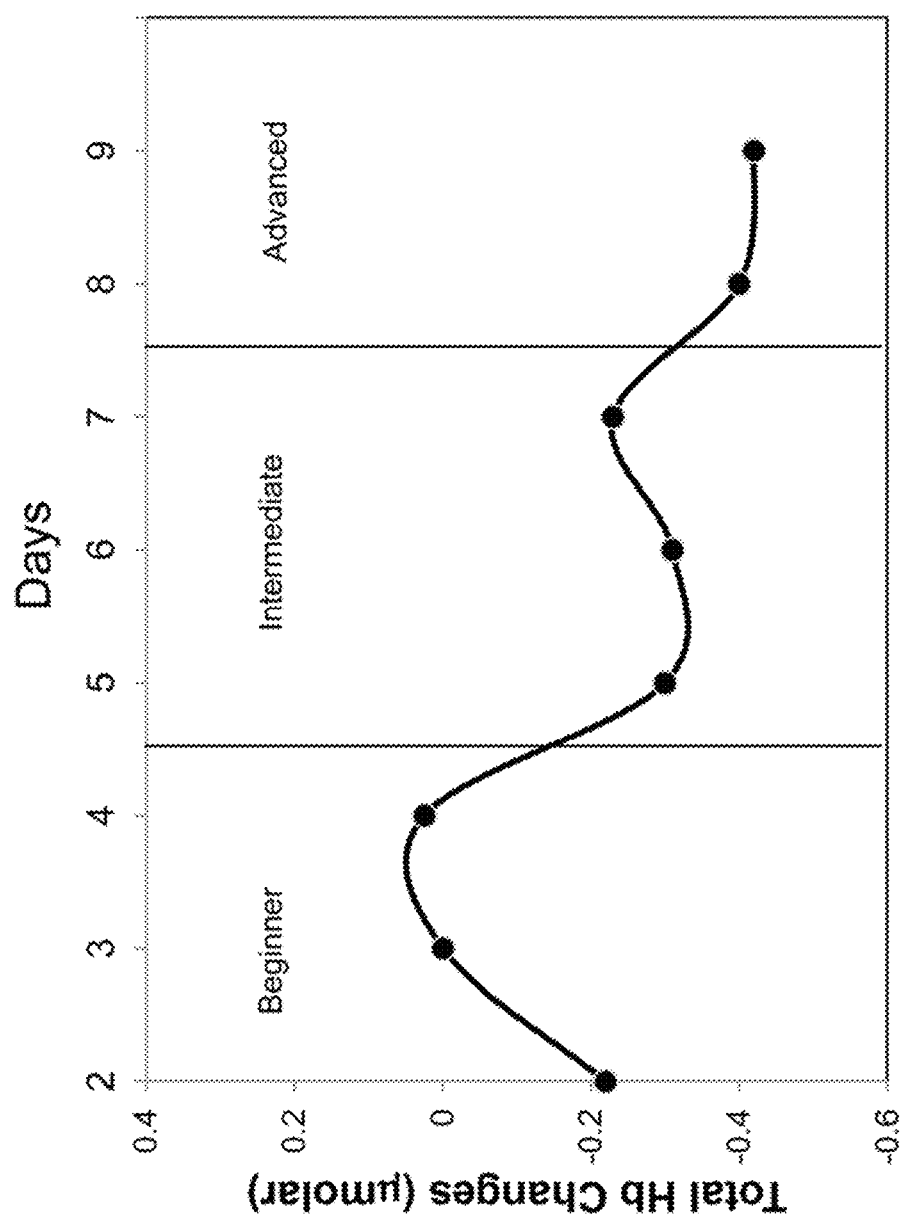
FIG. 10B illustrates that prefrontal cortex activity generally reduces over the course of behavioral training after an initial increase according to prior art.

FIGS. 10A and 10B illustrate phenotypic personalization and expertise training according to prior art. FIG. 10A depicts how the personalized adaptive method according to some embodiments of the present disclosure results in improved brain state induction for phenotypic subject categories. Initial brain states 1000 undergo an intervention stimulus 1002 to reach an optimal target brain state 1004. As non-limiting examples, the phenotypic subject categories of an optimal target brain state 1004 include a creative thinking group 1006 and an analytic thinking group 1008.

FIG. 10B iillustrates fNIRS pilot data showing that prefrontal cortex activity (indicative of mental effort on task) generally reduces over the course of 9 days of behavioral training, after an initial increase. This is interpreted as increasing efficiency with expertise (see Literature Reference No. 8). Prefrontal cortex activity is measured in total hemoglobin (Hb) changes.

Figure 11:
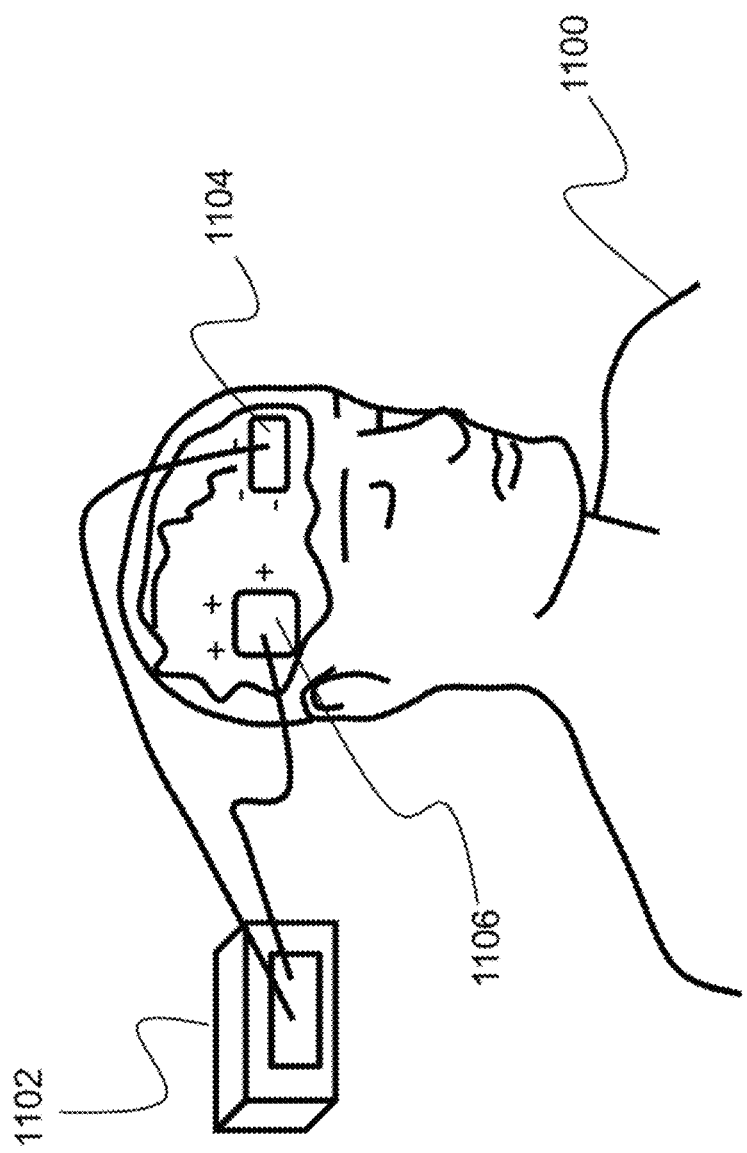
FIG. 11 illustrates a human subject receiving neurostimulation according to some embodiments of the present disclosure.

FIG. 11 illustrates a human subject 1100 receiving neurostimulation according to some embodiments of the present disclosure. A device 1102 able to generate an electrical current delivers neurostimulation by applying a current through one electrode 1104 (e.g., anode), and it flows through the brain to another electrode 1106 (e.g., cathode).

In the domain of unmanned aerial vehicles (UAV) teams, the discrepancy between added man-hours and higher accident rates has been partly attributed to individual operator fatigue, due to long operation shifts (e.g., typically 8+ hours), and operator boredom. The increased need for unmanned aerial vehicles in reconnaissance and combat operations has rapidly increased the demands, workloads, and hourly requirements of UAV pilots, operators, and support crew.

For example, the RQ-7 Shadow UAV requires 22 soldiers to operate effectively in the field. However, despite the added human effort, studies have shown that UAVs have three times the accident rate, and twice the cost of similar manned aircraft (see Literature Reference No. 61). UAV pilots often cite boredom and the required extended hours as reasons for quitting (see Literature Reference No. 63).

A second set of factors for the higher accident rates and increased demand on UAV teams can be attributed to inefficient team organization and performance. The effects of individual operator fatigue and boredom will compound and negatively influence team performance when an individual's state (especially a team leader) influences the team's states by decreasing performance through reduced team communication, role clarification, and objective/goal focus. Thus, there is an immediate and pressing need to increase UAV team performance by decreasing operator fatigue, enhancing team communication and understanding, and maintaining goal-oriented and adaptable team roles to focus individuals on the team's objective.

Neurostimulation enhancement of team performance according to the present disclosure has numerous domains of expected value and commercial applications, as well as military domains. For instance, UAV and pilot team enhancement training can be used to enhance operators' communication between individuals (in training, or as an operational system). Further, the present invention can be used to produce more effective UAV aircraft and systems requiring less man power and providing improved mission outcomes over current systems. Similarly, decreasing operator fatigue and enhancing team communication will facilitate leadership development and operability of those individuals.

Additionally, the present invention has applications in drive/operator/factory team training for enhanced human-human and human-machine/computer collaborations as well as worker injury preventions and avoidance. Furthermore, the method described herein has expected value for use in aircraft and operator team systems mentioned above. In addition, the present invention can facilitate combat team training and team performance, and reduce causalities/fatalities in combat situations with improved mission outcomes.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for augmenting team performance via neurostimulation, the system comprising:
   one or more processors and a non-transitory memory having instructions encoded thereon such that when the instructions are executed, the one or more processors perform operations of:
   selecting a target brain state in a subject;
   associating the target brain state with specific brain regions;
   determining a HD-tCS neurostimulation needed to reach the specific brain regions to induce the target brain state in the subject;
   applying the determined HD-tCS neurostimulation to the subject and sensing, via real-time neuroimaging from both electroencephalography (EEG) and functional near-infrared spectroscopy (fNIRS), neural activity of the subject while the subject performs a behavioral task;
   based on the sensed neural activity, adjusting the neurostimulation of the subject to move the subject into a target brain state; and
   personalizing a cognitive model for the subject by mapping a set of estimated cognitive capacities of the subject onto a set of parameters, and applying the set of parameters to the cognitive model.

2. The system as set forth in claim 1, wherein the one or more processors further perform operations of:
   generating an assessment of the subject while the subject is performing a behavioral task using neuroimaging data;
   detecting any behavioral performance deficiencies in the subject based on the assessment; and
   associating behavioral performance deficiencies with activation states in specific brain regions.

3. The system as set forth in claim 1, wherein the one or more processors further perform an operation of personalizing the cognitive model for the subject by:
   estimating the set of cognitive capacities of the subject from a set of diagnostic tests;
   predicting the subject's task performance and determining which tasks can be performed to improve the subject's task performance.

4. The system as set forth in claim 1, wherein the subject's brain state is synchronized with one or more other subjects, allowing all subjects to act in unison when performing tasks.

5. The system as set forth in claim 1, wherein if the sensed neural activity indicates a loss of focus in the subject, then the HD-tCS neurostimulation is adjusted to reach the specific brain regions needed to regain focus.

6. The system as set forth in claim 1, wherein the one or more processors further perform an operation of removing artifacts from a sensed EEG signal using a signal source separation method that uses parallel processing to separate maximally-independent sources of the sensed EEG signal by minimizing mutual information between source data channels.

7. The system as set forth in claim 1, wherein timing between HD-tCS neurostimulation and sensing via real-time neuroimaging is alternated to avoid interference.

8. The system as set forth in claim 1, wherein phenotypic subject categories of a target brain state comprise a creative thinking group and an analytic thinking group.

9. A computer-implemented method for augmenting team performance via neurostimulation, comprising:
  an act of causing one or more processors to execute instructions stored on a non-transitory memory such that upon execution, the one or more processors perform operations of:
    selecting a target brain state in a subject;
    associating the target brain state with specific brain regions;
    determining a HD-tCS neurostimulation needed to reach the specific brain regions to induce the target brain state in the subject;
    applying the determined HD-tCS neurostimulation to the subject and sensing, via real-time neuroimaging from both electroencephalography (EEG) and functional near-infrared spectroscopy (fNIRS), neural activity of the subject while the subject performs a behavioral task;
    based on the sensed neural activity, adjusting the neurostimulation of the subject to move the subject into a target brain state; and
    personalizing a cognitive model for the subject by mapping a set of estimated cognitive capacities of the subject onto a set of parameters, and applying the set of parameters to the cognitive model.

10. The method as set forth in claim 9, wherein the one or more processors further perform operations of:
  generating an assessment of the subject while the subject is performing a behavioral task using neuroimaging data;
  detecting any behavioral performance deficiencies in the subject based on the assessment; and
  associating behavioral performance deficiencies with activation states in specific brain regions.

11. The method as set forth in claim 9, wherein the one or more processors further perform an operation of personalizing the cognitive model for a subject by:
  estimating the set of cognitive capacities of the subject from a set of diagnostic tests;
  predicting the subject's task performance and determining which tasks can be performed to improve the subject's task performance.

12. The method as set forth in claim 9, wherein the subject's brain state is synchronized with one or more other subjects, allowing all subjects to act in unison when performing tasks.

13. The method as set forth in claim 9, wherein if the sensed neural activity indicates a loss of focus in the subject, then the HD-tCS neurostimulation is adjusted to reach the specific brain regions needed to regain focus.

14. The method as set forth in claim 9, wherein the one or more processors further perform an operation of removing artifacts from a sensed EEG signal using a signal source separation method that uses parallel processing to separate maximally-independent sources of the sensed EEG signal by minimizing mutual information between source data channels.

15. The method as set forth in claim 9, wherein timing between HD-tCS neurostimulation and sensing via real-time neuroimaging is alternated to avoid interference.

16. The method as set forth in claim 9, wherein phenotypic subject categories of a target brain state comprise a creative thinking group and an analytic thinking group.

17. A computer program product for augmenting team performance via neurostimulation, the computer program product comprising:
  computer-readable instructions stored on a non-transitory computer-readable medium that are executable by a computer having one or more processors for causing the processor to perform operations of:
    selecting a target brain state in a subject;
    associating the target brain state with specific brain regions;
    determining a HD-tCS neurostimulation needed to reach the specific brain regions to induce the target brain state in the subject;
    applying the determined HD-tCS neurostimulation to the subject and sensing, via real-time neuroimaging from both electroencephalography (EEG) and functional near-infrared spectroscopy (fNIRS), neural activity of the subject while the subject performs a behavioral task;
    based on the sensed neural activity, adjusting the neurostimulation of the subject to move the subject into a target brain state; and
    personalizing a cognitive model for the subject by mapping a set of estimated cognitive capacities of the subject onto a set of parameters, and applying the set of parameters to the cognitive model.

18. The computer program product as set forth in claim 17, further comprising instructions for causing the one or more processors to perform operations of:
  generating an assessment of the subject while the subject is performing a behavioral task using neuroimaging data;
  detecting any behavioral performance deficiencies in the subject based on the assessment; and
  associating behavioral performance deficiencies with activation states in specific brain regions.

19. The computer program product as set forth in claim 17, further comprising instructions for causing the one or more processors to perform an operation of personalizing the cognitive model for the subject by:
  estimating the set of cognitive capacities of the subject from a set of diagnostic tests;
  predicting the subject's task performance and determining which tasks can be performed to improve the subject's task performance.

20. The computer program product as set forth in claim 17, wherein the subject's brain state is synchronized with one or more other subjects, allowing all subjects to act in unison when performing tasks.

21. The computer program product as set forth in claim 17, wherein if the sensed neural activity indicates a loss of focus in the subject, then the HD-tCS neurostimulation is adjusted to reach the specific brain regions needed to regain focus.

22. The computer program product as set forth in claim 17, further comprising instructions for causing the one or more processors to further perform an operation of removing artifacts from a sensed EEG signal using a signal source separation method that uses parallel processing to separate maximally-independent sources of the sensed EEG signal by minimizing mutual information between source data channels.

23. The computer program product as set forth in claim 17, wherein timing between HD-tCS neurostimulation and sensing via real-time neuroimaging is alternated to avoid interference.

24. The computer program product as set forth in claim 17, wherein phenotypic subject categories of a target brain state comprise a creative thinking group and an analytic thinking group.

* * * * *